United States Patent [19]

Calverley et al.

[11] Patent Number: 5,206,229
[45] Date of Patent: Apr. 27, 1993

[54] VITAMIN D ANALOGUES

[75] Inventors: Martin J. Calverley, Herlev; Lise Binderup; Ernst T. Binderup, both of Tåstrup, all of Denmark

[73] Assignee: Leo Pharmaceutical Products LTD, Ballerup, Denmark

[21] Appl. No.: 582,944

[22] PCT Filed: Apr. 7, 1989

[86] PCT No.: PCT/DK89/00079
§ 371 Date: Oct. 10, 1990
§ 102(e) Date: Oct. 10, 1990

[87] PCT Pub. No.: WO89/10351
PCT Pub. Date: Nov. 2, 1989

[30] Foreign Application Priority Data

| Apr. 21, 1988 | [GB] | United Kingdom | 8809466 |
| Apr. 21, 1988 | [GB] | United Kingdom | 8809467 |
| Dec. 23, 1988 | [GB] | United Kingdom | 8830169 |
| Dec. 23, 1988 | [GB] | United Kingdom | 8830174 |

[51] Int. Cl.$^5$ .......................... A61K 31/59; C07J 9/00; C07C 35/06
[52] U.S. Cl. ................................. 514/167; 552/652; 552/653; 568/715; 568/808; 568/816; 568/817; 568/822; 568/838
[58] Field of Search ............... 568/817, 816, 718, 808, 568/823, 838, 822, 828, 824, 715; 514/167; 552/652, 653

[56] References Cited

U.S. PATENT DOCUMENTS 3,880,894  4/1975  De Luca et al.
4,206,131  6/1980  Salmond.

(List continued on next page.)

FOREIGN PATENT DOCUMENTS 171990    2/1986  European Pat. Off.
2607322   9/1976  Fed. Rep. of Germany.
2800782   7/1978  Fed. Rep. of Germany.

OTHER PUBLICATIONS

Etsuko Abe et al: "Differentiation of Mouse Myeloid Leukemia Cells Induced by 1α, 25-Dihydroxyvitamin (List continued on next page.)

*Primary Examiner*—Werren B. Lone
*Attorney, Agent, or Firm*—Cushman, Darby & Cushman

[57] ABSTRACT

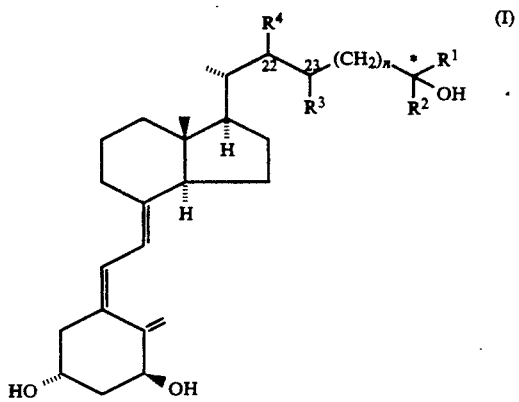

The present invention relates to compounds of formula (I), in which formula, n is an integer from 1-7; and $R^1$ and $R^2$, which may be the same or different, stand for hydrogen, or lower alkyl (but with the proviso that when n=1, $R^1$ and $R^2$ cannot simultaneously be hydrogen, nor can $R^1$ and $R^2$ simultaneously be an alkyl group independently chosen from methyl, ethyl and normal-propyl, and when n=2, $R^1$ and $R^2$ cannot simultaneously be methyl), or lower cyclo-alkyl, or, taken together with the carbon (starred in formula I) bearing the hydroxyl group, $R^1$ and $R^2$ can form a saturated or unsaturated $C_3$–$C_9$ carbocyclic ring; and $R^3$ and $R^4$ represent either simultaneously hydrogen, or when taken together constitute a bond, such that a double bond connects carbons 22 and 23; including diastereoisomeric forms (e.g. E or Z configuration of the 22,23-double bond; R or S configuration at the starred carbona atom) of the compounds of formula (I), in pure form or in mixtures. The present compounds find use in both the human and veterinary practice and show antiinflammatory and immuno-modulating effects as well as strong activity in inducing differentiation and inhibiting undesirable proliferation of certain cells, including cancer cells and skin cells.

10 Claims, No Drawings

U.S. PATENT DOCUMENTS

| | | |
|---|---|---|
| 4,267,117 | 5/1981 | Salmond . |
| 4,857,518 | 8/1989 | De Luca ............................ 514/167 |
| 4,891,364 | 1/1990 | Kubodera et al. ................. 514/167 |
| 4,898,855 | 2/1990 | Baggiolini et al. ................. 514/167 |

OTHER PUBLICATIONS

D3", Proc. Natl. Acad. Sci. USA, vol. 78, No. 8, (Aug. 1981); pp. 4990–4994.

Voula K. Ostrem et al: "24–and 26–Homo–1,25–Dihydroxyvitamin D3: Preferential Activity in Inducing Differentiation of Human Leukemia Cells HL–60 in Vitro", Proc. Natl. Acad. Sci. USA, vol. 84, (May 1987); pp. 2610–2614.

Lars Lind et al: "Blood Pressure is Lowered by Vitamin D (Alphacalcidol) During Long–Term Treatment of Patients with Intermittent Hypercalcaemia" Acta Med. Scand; vol. 222; (1987) pp. 423–427.

K. Muller et al: "1α,25–Dihydroxyvitamin D3 and a Novel Vitamin D Analogue MC 903 are Potent Inhibitors of Human Interleukin 1 in Vitro"; Immunology Letters, No. 17 (1988) pp. 361–366.

Lisa Binderup et al: "Effects of a Novel Vitamin D Analogue MC 903 on Cell Proliferation and Differentiation in Vitro and on Calcium Metabolism in Vivo"; Biochemical Pharmacology, vol. 37, No. 5, (1988) pp. 889–895.

Hiroshi Sai et al: "Synthesis of Some Side–Chain Homologues of 1α,25–Dihydroxyvitamin D3 and Investigation of Their Biological Activities", Chem. Pharm. Bull. vol. 34, No. 11, (1986) pp. 4508–4515.

Nobuo Ikeawa et al: "26,27–Diethyl–1A,25–Dihydroxyvitamin D3 and 24,24–Difluoro–24–Homo–1a,2-5–Dihydroxyvitamin D3: Highly Potent Inducer for Differentiation of Human Leukemia Cells HL–60", Chemical Pharmaceutical Bulletin; vol. 35, No. 10, (1987), pp. 4362–4365 (see particularly p. 4363).

M. J. Calverley, "Synthesis of MC 903, A Biologically Active Vitamin D Metabolite Analogue"—Tetrahedron, vol. 43, No. 20, (1987); pp. 4609–4619, (see particularly pp. 4609–4610).

Andrzej Kutner: "Novel Convergent Synthesis of Side–Chain–Modified Analogues of 1α,25–Dihydroxycholecalciferol and 1α,25–Dihydroxyergocalciferol 1", J. Org. Chem., 1988, 53, pp. 3450–3457, Chemical Abstracts, vol. 109, No. 7, (Aug. 1988); No. 55060u, Columbus, Ohio, US.

VITAMIN D ANALOGUES

This invention relates to a hitherto unknown class of compounds which shows antiinflammatory and immunomodulating effects as well as strong activity in inducing differentiation and inhibiting undesirable proliferation of certain cells, including cancer cells and skin cells, to pharmaceutical preparations containing these compounds, to dosage units of such preparations, and to their use in the treatment and prophylaxis of a number of disease states including diabetes mellitus, hypertension, imbalance in the immune system, inflammatory diseases such as rheumatoid arthritis and asthma as well as diseases characterized by abnormal cell differentiation and/or cell proliferation such as e.g. psoriasis and cancer.

The compounds of the invention constitute a novel class of vitamin D analogues and are represented by the general formula I

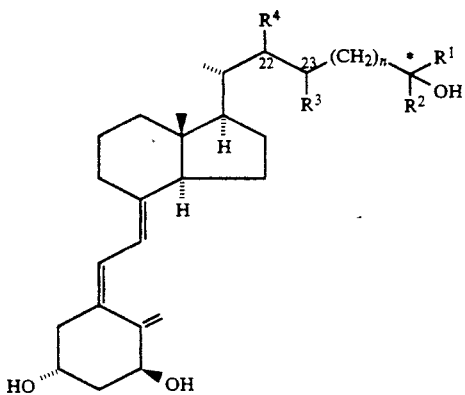

in which formula (and also throughout the remainder of this disclosure), n is an integer from 1-7; and $R^1$ and $R^2$, which may be the same or different, stand for hydrogen, or lower alkyl (but with the proviso that when n=1, $R^1$ and $R^2$ cannot simultaneously be hydrogen, nor can $R^1$ and $R^2$ simultaneously be an alkyl group independently chosen from methyl, ethyl and normal-propyl, and when n=2, $R^1$ and $R^2$ cannot simultaneously be methyl), or lower cyclo-alkyl, or, taken together with the carbon (starred in formula I) bearing the hydroxyl group, $R^1$ and $R^2$ can form a saturated or unsaturated $C_3$–$C_9$ carbocyclic ring; and $R^3$ and $R^4$ represent either simultaneously hydrogen, or when taken together constitute a bond, such that a double bond connects carbons 22 and 23. In the context of this invention, the expression "lower alkyl" indicates a straight or branched saturated or unsaturated carbon chain containing from 1 to 7 carbon atoms, and the expression "lower cyclo-alkyl" indicates a saturated or unsaturated $C_3$–$C_8$ carbocyclic ring.

As can be seen from formula I, depending on the meanings of $R^1$, $R^2$, $R^3$ and $R^4$, the compounds of the invention include diastereoisomeric forms (e.g. E or Z configuration of the 22,23-double bond; R or S configuration at the starred carbon atom). The invention covers all these diastereoisomers in pure form and also mixtures of diastereoisomers. It should be noted, however, that our investigations indicate a notable difference in activity between the stereoisomeric forms. In addition, derivatives of I in which one or more of the hydroxy groups are masked as groups which can be reconverted to hydroxy groups in vivo are also within the scope of the invention ("bioreversible derivatives or pro-drugs of I").

The term "bioreversible derivatives or prodrugs of I" includes, but is not limited to, derivatives of the compounds of formula I in which one or more hydroxy groups have been transformed into -O-acyl or -O-glycosyl or phosphate ester groups, such masked groups being hydrolyzable in vivo.

Also within the scope of this disclosure is another type of prodrug of I in which the hydroxyl group at the starred carbon atom is lacking. These compounds are relatively inactive in vitro, but are converted to active compounds of formula I by enzymatic hydroxylation after administration to the patient.

It has recently been shown that $1\alpha,25$-dihydroxy-vitamin $D_3$ ($1,25(OH)_2D_3$) influences the effects and/or production of interleukins (Immunol. Lett. 17, 361–366 (1988)), indicating the potential use of this compound in the treatment of diseases characterized by a dysfunction of the immune system, e.g. autoimmune diseases and rejection of transplants or other conditions characterized by an abnormal interleukin-1 production, e.g. inflammatory diseases such as rheumatoid arthritis and asthma.

It has also been shown that $1,25(OH)_2D_3$ is able to stimulate the differentiation of cells and inhibit excessive cell proliferation (Abe, E. et al, Proc. Natl. Acad. Sci., U.S.A. 78, 4990–4994 (1981)), and it has been suggested that this compound might be useful in the treatment of diseases characterized by abnormal cell proliferation and/or cell differentiation such as leukemia, myelofibrosis and psoriasis.

Also, the use of $1,25(OH)_2D_3$, or its pro-drug $1\alpha$-OH-$D_3$, for the treatment of hypertension (Lind, L. et al, Acta Med. Scand. 222, 423–427 (1987)) and diabetes mellitus (Inomata, S. et al, Bone Mineral 1, 187–192 (1986)) has been suggested.

However, the therapeutic possibilities in such indications of $1,25(OH)_2D_3$ are severely limited by the well known potent effect of this hormone on calcium metabolism; elevated blood concentrations will rapidly give rise to hypercalcemia. Thus, this compound and its potent synthetic analogues are not completely satisfactory for use as drugs in the treatment of e.g. psoriasis, leukemia or immune diseases which may require continuous administration of the drug in relatively high doses.

A number of vitamin D analogues have recently been described which show some degree of selectivity in favour of the cell differentiation inducing/cell proliferation inhibiting activity as compared with the effect on calcium metabolism.

Thus, the vitamin $D_3$ analogue, MC 903, containing a 22,23-double bond, a 24-hydroxy group and in which the carbon atoms 25,26 and 27 are incorporated in a three membered ring, is a potent inducer of cell differentiation and inhibitor of cell proliferation which shows only moderate activity on calcium metabolism in vivo (Binderup, L. and Bramm, E., Biochemical Pharmacology 37, 889–895 (1988)). However, this selectivity is not paralleled by in vitro studies, which show that MC 903 binds equally well as $1,25(OH)_2D_3$ to the intestinal vitamin D receptor. It may therefore be that the low in vivo activity on calcium metabolism of MC 903 is due to a rapid metabolism of the compound, thus limiting the potential of this compound for systemic use.

24-Homo-1,25-dihydroxyvitamin $D_3$ and 26-homo-1,25-dihydroxyvitamin $D_3$ (together with their 22,23-didehydroanalogues) (Ostrem, V. K.; Tanaka, Y.; Prahl, J.; DeLuca, H. F.; and Ikekawa, N.; Proc. Natl. Acad. Sci. USA 84, 2610-14 (1987)) have been claimed to have the same binding affinity as $1,25(OH)_2D_3$ to both the rat and chicken intestinal receptor and the receptor in a human myeloid leukemia cell line (HL-60), and yet to be 10-fold more potent than $1,25(OH)_2D_3$ in inducing differentiation of HL-60 cells in vitro. In vivo, these compounds are respectively "significantly less potent" and "more potent" than $1,25(OH)_2D_3$ in calcium metabolism assessments.

26,27-Dimethyl-1α,25-dihydroxyvitamin $D_3$ has been synthesized, but the published information regarding its biological activities is contradictory. (Sai, H.; Takatsuto, S.; Hara, N.; and Ikekawa, N.; Chem. Pharm. Bull. 33, 878-881 (1985) and Ikekawa, N.; Eguchi, T.; Hara, N.; Takatsuto, S.; Honda, A.; Mori, Y.; and Otomo, S.; Chem. Pharm. Bull. 35, 4362-4365 (1987)). The closely related 26,27-diethyl-1α,25-dihydroxyvitamin $D_3$ is also reported by these authors; in this case as having "almost no vitamin D activity" (i.e. calcium metabolism effects) while being 10-fold more potent than $1,25(OH)_2D_3$ in inducing cell differentiation.

The fact that there are only small structural differences between the above compounds indicates that the present state of knowledge does not allow prediction of the structure of vitamin D analogues which will show a favourable degree of selectivity, as reflected by a higher cell differentiating activity in vitro compared to the binding affinity for intestinal vitamin D receptor in vitro. Furthermore, the matter is complicated by the observation that receptor binding affinities in vitro are not always paralleled by in vivo studies, probably reflecting a pharmacokinetic difference between the compounds.

Surprisingly, it has now been found that the compounds of the present invention compared to the above mentioned known compounds show a higher degree of separation of the biological effect on cell diffentiation/proliferation and interleukin I activity on the one side and on calcium metabolism on the other side.

The selectivity of the compounds is illustrated by the fact that while the concentration needed to induce cell differentiation in a human monocytic tumour cell line is the same as or lower than that needed of $1,25(OH)_2D_3$ to give the same effect, their binding affinity for the intestinal receptor is much lower than that of $1,25(OH)_2D_3$. In rats the compounds are considerably less active than $1,25(OH)_2D_3$ in inducing hypercalciuria and hypercalcemia. Thus for example compounds 36, 37, 38, and 54 (see Table 2) have binding affinities for the intestinal receptor which are between 1% and 10% of that of $1,25(OH)_2D_3$, in good agreement with the observed lower in vivo potency on calcium metabolism. The same compounds have high affinities for the receptor in tumour cells (similar to that of $1,25(OH)_2D_3$) and furthermore are effective in inducing differentiation and inhibiting proliferation of these cells at the same low concentrations as $1,25(OH)_2D_3$.

At the same time the compounds of the invention show good bioavailability as well as chemical and metabolic stability, rendering them especially suited for both local and systemic treatment and prophylaxis of human and veterinary disorders which are characterized by 1) abnormal cell proliferation and/or cell differentiation, such as certain dermatological disorders including psoriasis and certain cancer forms, 2) an imbalance in the immune system, e.g. autoimmune diseases, including diabetes mellitus and rejection of transplants or 3) inflammatory diseases, such as rheumatoid arthritis and asthma.

The present compounds may be used in combination with other pharmaceuticals. In the prevention of graft rejection, a treatment with the present compounds may advantageously be combined with e.g. a cyclosporin treatment.

Compounds I can be conveniently prepared from vitamin $D_2$ via the closely related intermediates 1 (Tetrahedron Letters, 1987, 28, 1337) and 2 (Tetrahedron, 1987, 43, 4609) by the routes outlined in Scheme 2. A key step in the synthesis as described is the reaction with a side chain fragment (of type A, B or C) either directly (type A) or after treatment of the side chain fragment (type B or C) with strong base (such as n-butyl-lithium or lithium di-iso-propylamide) to generate a nucleophilic reagent (of type B' or C', respectively). All these types of reactions are well known in the art of carbon-carbon bond formation in synthetic organic chemistry, and have in fact been applied in syntheses of other vitamin D-type compounds.

In general, the side chain fragment has the structure

$$Z-(CH_2)_n-C(R^1)(R^2)-OR^5$$

with the following meanings (the following standard abbreviations are used throughout this disclosure: Et=ethyl; Hep=heptyl; Me=methyl; Ph=phenyl; Pr=propyl; THP=tetrahydro-4H-pyran-2-yl; THF=tetrahydrofuran; Ts=p-toluenesulphonyl):

For type A, $Z=X-CH_2-$, where X is a leaving group, e.g. Br, I, or TsO.

For type B, $Z=PhS(O_2)-CH_2-$, and the corresponding B' has $Z=PhS(O_2)-CHM-$, where M=metal, e.g. Li.

For type C, $Z=Ph_3P^+-CH_2-$ or $Z=Q_2P(O)-CH_2-$, where Q=methoxy, ethoxy or phenyl, and the corresponding C' has $Z=Ph_3P^+-CH-$ or $Q_2P(O)-CHM-$ (M=metal e.g. Li).

$R^5$ is optionally hydrogen (not in A) or an alcohol protective group such as tri(loweralkyl)silyl or THP. In the case where $R^5=H$ in B or C, then $R^5=M$ (M=metal, e.g. Li) in the derived B' or C'.

The syntheses of the particular fragments of types A, B and C can be varied greatly, but solely for the purpose of exemplification, the syntheses of the specific compounds shown in Table 1 using the routes summarized in Scheme 1 are described in the Preparations. It should be noted that the fragments of types B and C, with n, $R^1$, $R^2$ and $R^5$ corresponding to an exemplified type A compound, but which are not exemplified themselves, are readily obtained from the corresponding described intermediates by analogous reactions.

TABLE 1

| Compound Number+ | Some Specific Side Chain Fragments $[Z-(CH_2)_n-C(R^1)(R^2)OR^5]$ Formula | | | | | |
|---|---|---|---|---|---|---|
| | Type* | n | $R^1$ | $R^2$ | $R^5$ | Z |
| 3 | A | 1 | $-(CH_2)_2-$ | | $SiMe_3$ | $BrCH_2$ |
| 4 | A | 1 | $-(CH_2)_2-$ | | THP | $TsOCH_2$ |
| 5 | A | 1 | $-(CH_2)_4-$ | | $SiMe_3$ | $BrCH_2$ |
| 6 | A | 1 | $-(CH_2)_5-$ | | $SiMe_3$ | $BrCH_2$ |
| 7 | A | 2 | $-(CH_2)_2-$ | | $SiMe_3$ | $BrCH_2$ |
| 8 | A | 3 | Me | Me | $SiMe_3$ | $BrCH_2$ |
| 9 | A | 3 | Et | Et | $SiMe_3$ | $BrCH_2$ |

TABLE 1-continued

Some Specific Side Chain Fragments
[Z—(CH$_2$)$_n$—C(R$^1$)(R$^2$)OR$^5$]

| Compound Number+ | Type* | n | R$^1$ | R$^2$ | R$^5$ | Z |
|---|---|---|---|---|---|---|
| 10 | A | 4 | Me | Me | SiMe$_3$ | BrCH$_2$ |
| 11 | A | 5 | Me | Me | SiMe$_3$ | BrCH$_2$ |
| 12 | B | 1 | —(CH$_2$)$_2$— | | THP | PhS(O$_2$)CH$_2$ |
| 13 | B | 4 | Me | Me | H | PhS(O$_2$)CH$_2$ |
| 14 | C | 4 | Me | Me | H | Ph$_2$P(O)CH$_2$ |
| 15a++ | A | 1 | Me | H | SiMe$_3$ | ICH$_2$ |
| 15b** | A | 1 | H | Me | SiMe$_3$ | ICH$_2$ |
| 16** | A | 1 | H | Hep | SiMe$_3$ | ICH$_2$ |
| 17 | A | 2 | Et | Et | SiMe$_3$ | BrCH$_2$ |
| 18 | A | 3 | Pr | Pr | SiMe$_3$ | BrCH$_2$ |
| 19 | B | 3 | Me | Me | H | PhS(O$_2$)CH$_2$ |
| 60 | A | 2 | Pr | Pr | SiMe$_3$ | BrCH$_2$ |

+ As referred to in the Preparations
* See text
++ S-Form
** R-Form

TABLE 2

Some Specific Examples of Compounds Indicated on Scheme 2 which are Referred to by Number in the Preparations and Examples

| Compound Number | | n | R$^1$ | R$^2$ | R$^3$ or R$^6$ | R$^4$ or R$^7$ | R$^5$ |
|---|---|---|---|---|---|---|---|
| 20a, 20b | II | 1 | —(CH$_2$)$_2$— | | H | SeMe | SiMe$_3$ |
| 21a, 21b | II | 1 | —(CH$_2$)$_2$— | | H | SeMe | H |
| 22 | II | 1 | —(CH$_2$)$_2$— | | H | SeMe | THP |
| 23 | III | 1 | —(CH$_2$)$_2$— | | H | H | THP |
| 24 | III | 1 | —(CH$_2$)$_5$— | | H | H | H |
| 25 | III | 3 | Me | Me | H | H | H |
| 26 | III | 4 | Me | Me | H | H | H |
| 27 | III | 4 | Me | Me | Bond (22E) | | H |
| 28 | IV | 1 | —(CH$_2$)$_2$— | | H | H | THP |
| 29 | IV | 1 | —(CH$_2$)$_5$— | | H | H | H |
| 30 | IV | 3 | Me | Me | H | H | H |
| 31 | IV | 4 | Me | Me | H | H | H |
| 32 | IV | 4 | Me | Me | Bond (22E) | | H |
| 33 | V | 1 | —(CH$_2$)$_2$— | | H | H | THP |
| 34 | I | 1 | —(CH$_2$)$_2$— | | H | H | — |

SCHEME 1

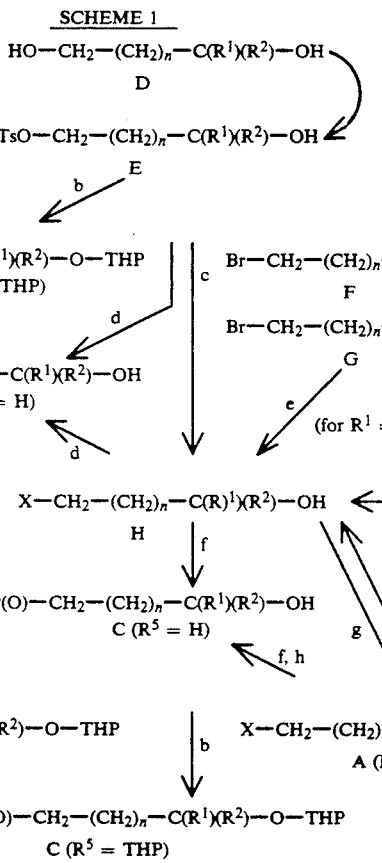

Notes to Scheme 1
a. TsCl - base;
b. dihydropyran - acid;
c. LiBr (for X = Br) or NaI (for X = I);
d. (i) PhSH - base, (ii) H$_2$O$_2$ - NaWO$_4$;
e. Grignard reagent R$^1$MgBr or R$^1$MgI;
f. (i) Ph$_2$P$^-$Li$^+$, (ii) H$_2$O$_2$;
g. Me$_3$SiCl - base;
h. MeOH - acid;

Some of these side chain fragments are converted (see Preparations and Examples) to the appropriate compounds I via the intermediates indicated on Scheme 2. The intermediates are specified in Table 2 together with the exemplified compounds I.

| 35 | I | 1 | —(CH$_2$)$_5$— | | H | H | — |
|---|---|---|---|---|---|---|---|
| 36 | I | 3 | Me | Me | H | H | — |
| 37 | I | 4 | Me | Me | H | H | — |
| 38 | I | 4 | Me | Me | Bond (22E) | | — |
| 39+ | III | 1 | Me | H | H | H | H |
| 40* | III | 1 | H | Me | H | H | H |
| 41* | III | 1 | H | Hep | H | H | H |
| 42 | III | 3 | Me | Me | Bond (22E) | | H |
| 43 | III | 3 | Et | Et | H | H | H |

TABLE 2-continued

Some Specific Examples of Compounds Indicated on Scheme 2 which are Referred to by Number in the Preparations and Examples

| Compound Number | n | $R^1$ | $R^2$ | $R^3$ or $R^6$ | $R^4$ or $R^7$ | $R^5$ |
|---|---|---|---|---|---|---|
| 44 | III | 3 | Pr | Pr | H | H | H |
| 45+ | IV | 1 | Me | H | H | H | H |
| 46* | IV | 1 | H | Me | H | H | H |
| 47* | IV | 1 | H | Hep | H | H | H |
| 48 | IV | 3 | Me | Me | Bond (22E) | H |
| 49 | IV | 3 | Et | Et | H | H | H |
| 50 | IV | 3 | Pr | Pr | H | H | H |
| 51+ | I | 1 | Me | H | H | H | — |
| 52* | I | 1 | H | Me | H | H | — |
| 53* | I | 1 | H | Hep | H | H | — |
| 54 | I | 3 | Me | Me | Bond (22E) | — |
| 55 | I | 3 | Et | Et | H | H | — |
| 56 | I | 3 | Pr | Pr | H | H | — |
| 57 | III | 2 | Et | Et | H | H | H |
| 58 | IV | 2 | Et | Et | H | H | H |
| 59 | I | 2 | Et | Et | H | H | — |
| 63 | III | 2 | Pr | Pr | H | H | SiMe3 |
| 64 | IV | 2 | Pr | Pr | H | H | SiMe3 |
| 65 | I | 2 | Pr | Pr | H | H | — |

+S-Configuration at starred carbon atom
*R-Configuration at starred carbon atom

Notes to Table 2
In compounds of formula II there is the possibility for diastereoisomers at C-23 and/or C-22. These have been separated in some instances for characterisation, but in most cases, the unpurified reaction products II were used directly as a mixture in subsequent steps; data is not provided for these intermediates, nor do these compounds appear in Table 2.

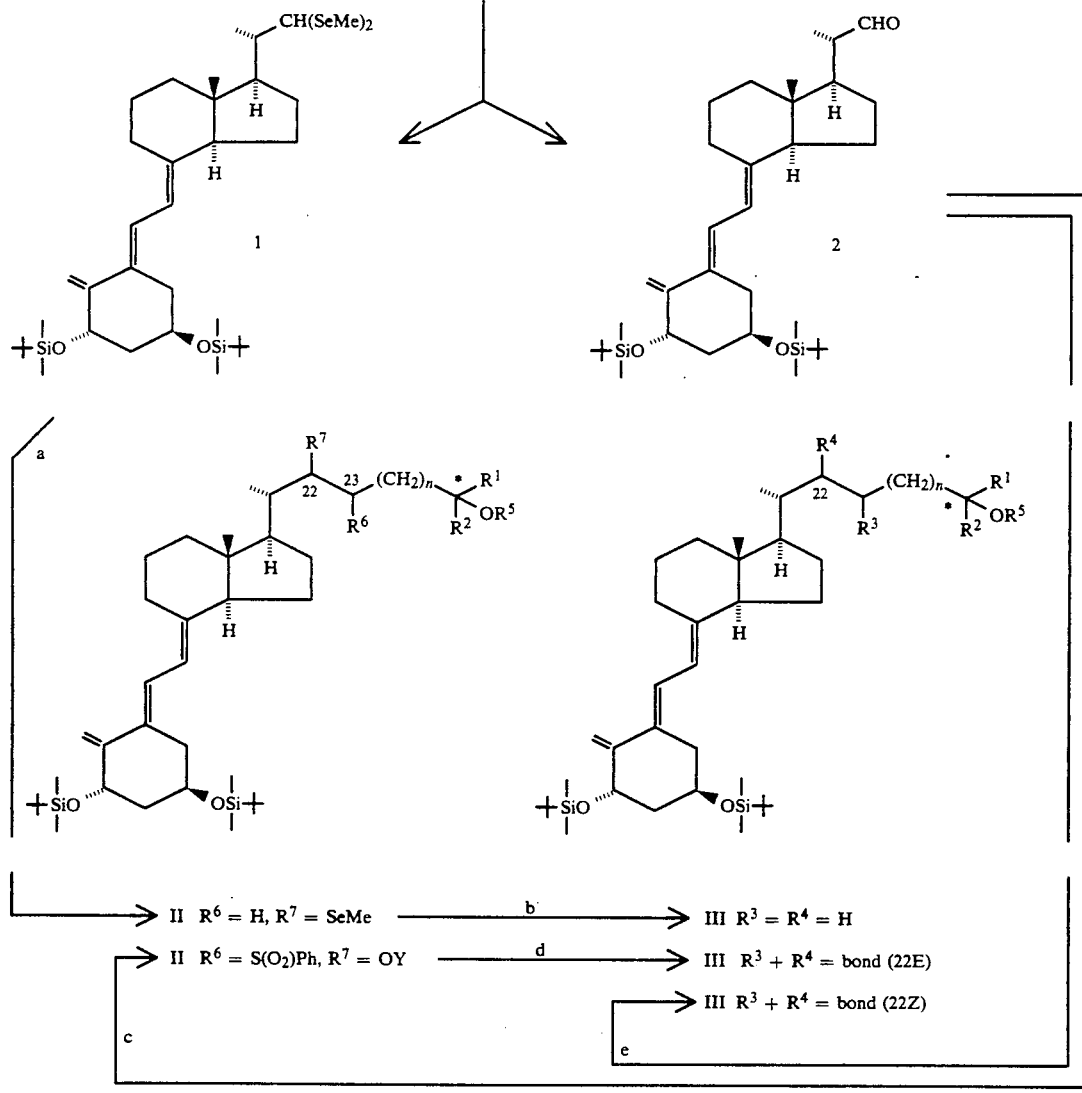

SCHEME 2

-continued
SCHEME 2

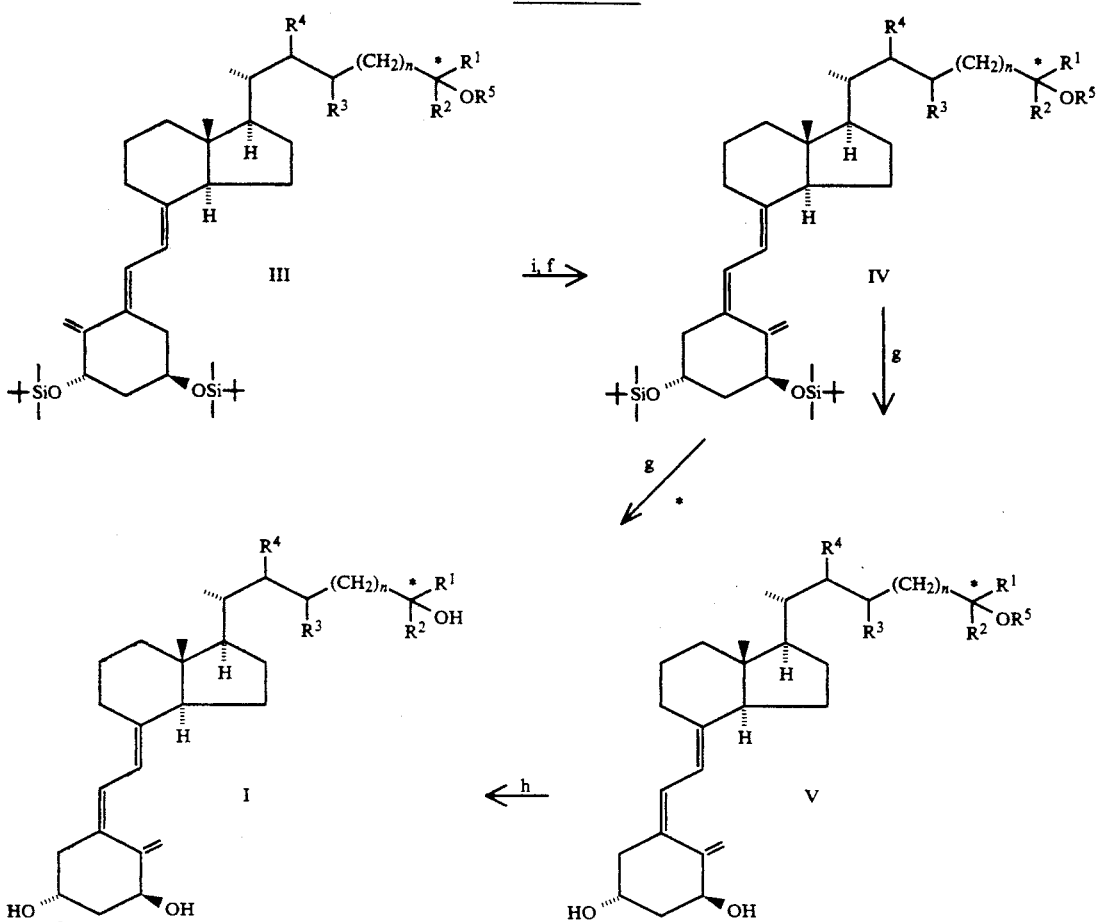

*For $R^5$ = H or tri-alkylsilyl
Notes to Scheme 2

$R^5$ is optionally H or an alcohol protective group, and the meaning of $R^5$ can be changed at different stages of the synthesis of a particular compound I. Y is optionally H or a derivatising group chosen to facilitate step "d."

a. (i) n-BuLi, (ii) Side chain fragment A (see text);

b. (i) $SO_2$, (ii) n-$Bu_3$SnH - hv, (iii) $NaHCO_3$ (boiling EtOH);

c. Metallated derivative (B') of side chain fragment B (see text), (ii) Optional derivatisation either in situ of the intermediate 22-alkoxide or after isolation of the 22-hydroxy-compound;

d. Reductive elimination mediated by e.g. Na—Hg (for Y = H, MeC(O)—, PhC(O)— or MeS($O_2$)—), or the same conditions as described above for step "b" (for Y = MeS—C(S)— or PhC(S)—);

e. (i) Wittig (Horner-Wittig) reagent, reagent (C') derived from side chain fragment C (see text) by treatment with n-BuLi,
(ii) aqueous work-up, (iii) NaH (ii and iii only for the $Q_2$P(O)-type reagent);

f. hv - triplet sensitizer;

g. n-$Bu_4N^+F^-$ or HF;

h. Any necessary reaction (sequence) for deprotecting the side chain OH group. This step may optionally be performed at an earlier stage in the synthesis;

i. In the event that $R^1 \neq R^2$, and $R^5$ = H, optional inversion of the configuration at the starred carbon atom e.g. via Mitsunobu's reaction (Synthesis, 1981, 1).

Parallel reactions can be used to convert other side chain fragments to the corresponding compounds I. It can be seen that the routes of Scheme 1 are very flexible and facilitate the synthesis of side chain fragments wherein n, $R^1$ and $R^2$ can take any of the meanings stipulated in the description of formula I. For the synthesis of compounds I in which the starred carbon atom is chiral ($R^1 \neq R^2$), the compound D in Scheme 1 is conveniently used as the stereoisomer with largely or exclusively the required configuration, to give largely or exclusively the required diastereoisomer(s) of I.

Alternatively, the compound D may be used as the stereoisomer having the opposite configuration, and the configuration may be then inverted at a later stage in the synthesis.

One method for preparing D in high stereochemical purity for the case where $R^1$=H is shown in Scheme 3.

SCHEME 3

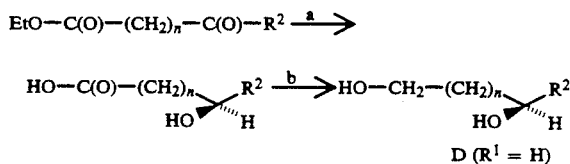

a. (i) KOH, (ii) Saccharomyces cerevisiae, glucose, pH 6-7;
b. (i) $CH_2N_2$, (ii) $LiAlH_4$.

The synthesis of the prodrugs of compounds I which lack the side chain hydroxyl (at the starred carbon atom) may follow the routes of Scheme 2, using the appropriate side chain fragment of structure Z—(CH$_2$)$_n$—CH(R$^1$)(R$^2$).

Thus, the prodrug forms corresponding to Compounds 36 and 54 are prepared from the BrCH$_2$(CH$_2$)$_3$CHMe$_2$ [used as side chain fragment A or as the derived fragment B (PhS(O$_2$)CH$_2$(CH$_2$)$_3$CHMe$_2$) respectively], and those corresponding to compounds 37 and 38 similarly from BrCH$_2$(CH$_2$)$_4$CHMe$_2$.

In an alternative synthetic route to compounds III (R$^3$=R$^4$=H) (or the corresponding side chain desoxy analogue), the aldehyde 2 is reduced (sodium borohydride in ethanol) to the corresponding primary alcohol (compound 61 of the Preparations), which is then converted to the tosylate (compound 62 of the preparations) (p-toluenesulphonyl chloride in pyridine). This compound is then coupled in the presence of dilithium tetrachlorocuprate with the Grignard reagent derived from requisite side chain fragment A [or the corresponding desoxy analogue, Z—(CH$_2$)$_n$—CH(R$^1$)(R$^2$)] (in which Z=BrCH$_2$ or ICH$_2$) by reaction with magnesium metal in THF. The synthesis of compound 65 and of the side chain desoxy analogue of compound 36 (compound 68) via this procedure is exemplified.

The present compounds are intended for use in pharmaceutical compositions which are useful in the treatment of human and veterinary disorders as described above.

The amount required of a compound of formula I (hereinafter referred to as the active ingredient) for therapeutic effect will, of course, vary both with the particular compound, the disease state which is to be treated, the route of administration and the mammal under treatment. The compounds of the invention can be administered by the parenteral, intra-articular, enteral or topical routes. They are well absorbed when given enterally and this is the preferred form of administration in the treatment of systemic disorders.

Conveniently, the active ingredient comprises from 1 ppm to 0.1% for topical formulations and 1 ppm to 1% for oral and parenteral formulations, calculated by weight of the formulation.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations, both for veterinary and for human medical use, of the present invention comprise an active ingredient in association with a pharmaceutically acceptable carrier therefore and optionally other therapeutic ingredient(s). The carrier(s) must be "acceptable" in the sense of being compatible with the other ingredients of the formulations and not deleterious to the recipient thereof.

The formulations include e.g. those in a form suitable for oral, rectal, parenteral (including transdermal, subcutaneous, intramuscular and intravenous), intra-articular and topical administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

A tablet may be made by compressing or moulding the active ingredient optionally with one or more accessory ingredients. Compressed tablets may be prepared by compressing, in a suitable machine, the active ingredient in a free-flowing form such as a powder or granules, optionally mixed by a binder, lubricant, inert diluent, surface active or dispersing agent. Moulded tablets may be made by moulding, in a suitable machine, a mixture of the powdered active ingredient and suitable carrier moistened with an inert liquid diluent.

Formulations for rectal administration may be in the form of a suppository incorporating the active ingredient and a carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra-articular and ophthalmic administration.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For asthma treatment, inhalation of powder, self-propelling or spray formulations, dispensed with a spray can, a nebulizer or an atomizer can be used. The formulations, when dispensed, preferably have a particle size in the range of 10 to 100$\mu$.

Such formulations are most preferably in the form of a finely comminuted powder for pulmonary administration from a powder inhalation device or self-propelling powder-dispensing formulations. In the case of self-propelling solution and spray formulations, the effect may be achieved either by choice of a valve having the desired spray characteristics (i.e. being capable of producing a spray having the desired particle size) or by incorporating the active ingredient as a suspended powder in controlled particle size. These selfpropelling formulations may be either powder-dispensing formulations or formulations dispensing the active ingredient as droplets of a solution or suspension.

Self-propelling powder-dispensing formulations preferably comprise dispersed particles of solid active ingredients, and a liquid propellant having a boiling point below 18° C. at atmospheric pressure. The liquid propellant may be any propellant known to be suitable for medicinal administration and may comprise one or more C$_1$–C$_6$-alkyl hydrocarbons or halogenated C$_1$–C$_6$-alkyl hydrocarbons or mixtures thereof; chlorinated and fluorinated $C_1$-$C_6$-alkyl hydrocarbons are especially preferred. Generally, the propellant constitutes 45 to 99.9% w/w of the formulation whilst the active ingredient constitutes 1 ppm to 0.1% w/w, of the formulation.

In addition to the aforementioned ingredients, the formulations of this invention may include one or more additional ingredients such as diluents, buffers, flavouring agents, binders, surface active agents, thickeners, lubricants, preservatives, e.g. methyl hydroxybenzoate (including anti-oxidants), emulsifying agents and the like.

The compositions may further contain other therapeutically active compounds usually applied in the treatment of the above mentioned pathological conditions.

The present invention further concerns a method for treating patients suffering from one of the above pathological conditions, said method consisting of administering to a patient in need of treatment an effective amount of one or more compounds of formula I, alone or in combination with one or more other therapeutically active compounds usually applied in the treatment of said pathological conditions. The treatment with the present compounds and/or with further therapeutically active compounds may be simultaneous or with intervals.

In the treatment of systemic disorders daily doses of from 1-1000 μg, preferably from 2-250 μg, of a compound of formula I are administered. In the topical treatment of dermatological disorders, ointments, creams or lotions containing from 1-1000 μg/g, and preferably from 10-500 μg/g, of a compound of formula I are administered. The oral compositions are formulated, preferably as tablets, capsules, or drops, containing from 0.5-500 μg, preferably from 1-250 μg, of a compound of formula I, per dosage unit.

The invention will now be further described in the following non-limiting Preparations and Examples:

PREPARATIONS AND EXAMPLES

General

The compounds referred to in the Preparations and Examples are to be identified by number or letter with the corresponding formulae in the Schemes and/or Tables. Ultra-violet spectra (λ) were measured for solutions in 96% ethanol. For nuclear magnetic resonance spectra chemical shift values (δ) are quoted in p.p.m. for deuteriochloroform solutions relative to internal tetramethylsilane (δ=0) or chloroform (δ=7.25). The value for a multiplet, either defined (doublet (d), triplet (t), quartet (q)) or not (m) at the approximate mid point is given unless a range is quoted (s=singlet, b=broad). Coupling constants (J) are given in Hertz, and are approximated to the nearest unit.

Ether is diethyl ether, and was dried over sodium. THF was dried over sodium-benzophenone. Petroleum ether refers to the pentane fraction. Brine is saturated sodium chloride solution. All solutions referred to are aqueous, unless otherwise indicated. Organic solutions were dried over dried magnesium sulphate and concentrated on a rotary evaporator at water aspirator pressure.

PREPARATION 1

1-(2-Hydroxyethyl)cyclopropanol [D (n=1, $R^1+R^2$=—$(CH_2)_2$—)]

A stirred solution of lithium di-iso-propylamide (prepared by the slow adition of n-butyl-lithium solution (1.5M i hexane, 146 ml) to di-iso-propylamine (30.8 ml) in dried THF (200 ml) at 0° C.) was cooled to −70° C. and treated dropwise with freshly distilled 4-hydroxy-2-butanone (8.4 g) at such a rate that the temperature of the reaction mixture remained below −65° C. After a further 20 minutes a solution of trimethylsilyl chloride (38 ml) and triethylamine (10 ml) in dried THF (50 ml) (prepared at 0° C., and then cooled to about −60° C.) was added over ca. one minute via a double tipped needle, after which the temperature of the reaction mixture rose momentarily to −50° C., but fell again to −70° C. After being kept for a further 1 hour at this temperature (during which time a white precipitation occurred), the reaction mixture was allowed to warm over 2 hours to room temperature before it was partitioned between petroleum ether (1 l) and 2% sodium hydrogen carbonate solution (400 ml). The organic layer was separated, washed with brine, and dried. Removal of the solvent in vacuo gave a residue which was purified by distillation to give an oil, b.p. 71°-73° C./11 mmHg (Found: C, 51.83; H, 10.54. $C_{10}H_{24}O_2Si_2$ requires C, 51.67; H, 10.41%). The $^1H$ NMR spectrum showed the product to be a ca. 85:15 mixture of 2,4-bis(-trimethylsilyloxy)-1-butene and 2,4-bis(trimethyl-silyloxy)-2-butene, and this mixture was used as such in the next step.

Zinc granules (3.6 g) were converted to a silver couple by treatment for 30 seconds with a solution of silver acetate (30 mg) in acetic acid (20 ml) at 80° C. After decantation, the zinc-silver couple was washed by decantation 6 times with 15 ml dried ether and finally covered with ether (40 ml). To this mixture, stirred and heated under reflux under a nitrogen atmosphere, was added di-iodomethane (7.5 g) dropwise over 5 minutes. Heating under reflux continued for 1 hour before the additon dropwise via a syringe of the kinetic mixture of 2,4-bis(trimethylsilyloxy)-1- and -2-butenes described above (4.7 g). After a further 20 hours reflux, the stirred reaction mixture was ice-cooled and treated dropwise with pyridine (4.8 ml), diluted with more dry ether and filtered. The filtrate was concentrated in vacuo to give an oil which was purified by chromatography (200 g silica gel; 3% ether in petroleum ether as eluant) to give 2-(1-trimethylsilyloxycyclopropyl)ethoxytrimethylsi-lane as an oil which was used directly in the next step. Distillation (b.p. 80°-81° C./10 mmHg) afforded an analytical sample (Found: C, 53.61; H, 10.58. $C_{11}H_{26}O_2Si_2$ requires C, 53.60; H, 10.63%).

To an ice-cooled solution of 2-(1-trimethylsilyloxycyclopropyl)ethoxytrimethylsilane (3.15 g) in methanol (20 ml) was added methanolic hydrogen chloride (ca. 1M, 0.1 ml). After 10 minutes, the solution was concentrated in vacuo (at room temperature) to constant weight to give the title compound as an oil, δ (100 MHz) 0.47 (2H, m), 0.77 (2H, m), 1.77 (2H, t, J 6), 3.35 (1H, bs), 3.9 [3H, m, including 3.92 (2H, t, J 6)]. An analytical sample was prepared by distillation, b.p. 58°-59° C./0.1 mmHg (Found: C, 58.92; H, 9.83. $C_5H_{10}O_2$ requires C, 58.80; H, 9.87%).

PREPARATION 2

1-(2-Bromoethyl)cyclopropyloxytrimethylsilane (Compound 3)

To an ice-cooled solution of 1-(2-hydroxyethyl)cyclopropanol (1.31 g) and pyridine (4 ml) in dichloromethane (20 ml) was added p-toluenesulphonyl chloride (4.7 g). The mixture was then stirred at room temperature under an atmosphere of nitrogen for 5 hours before being partitioned between ether (100 ml) and water. The organic layer was washed consecutively with 1N hydrochloric acid, water, 5% sodium hydrogen carbonate solution, and brine, and dried. Concentration in vacuo gave a residue which was purified by chromatography (150 g silica gel; 40% ethyl acetate in petroleum ether as eluant) to give the 1-(2-p-toluenesulphonyloxyethyl)cyclopropanol [E; n=1, $R^1+R^2=-(CH_2)_2-$] as an oil.

A stirred solution of lithium bromide (15 g) and 1-(2-p-toluenesulphonyloxyethyl)cyclopropanol (3.15 g) in acetone (80 ml) was heated under reflux for 1 hour. The cooled reaction mixture was partitioned between dichloromethane (200 ml) and water, and the aqueous phase extracted with more dichloromethane. The combined dichloromethane-phases were washed with water and brine. After drying, removal of the solvent in vacuo gave 1-(2-bromoethyl)cyclopropanol [H; n=1, $R^1+R^2=-(CH_2)_2-$] as an oil. Distillation of a portion gave an analytical sample, b.p. 32° C./0.2 mmHg (Found: C, 36.55; H, 5.67. $C_5H_9OBr$ requires C, 36.39; H, 5.50%).

To an ice-cooled solution of 1-(2-bromoethyl)cyclopropanol (1.4 g), triethylamine (2.8 ml) and 4-dimethylaminopyridine (0.1 g) in dichloromethane (25 ml) stirred under a nitrogen atmosphere was added dropwise trimethylsilyl chloride (1.9 ml). After a further 40 minutes stirring on the ice bath, the reaction mixture was partitioned between ether (100 ml) and water. The organic layer was washed consecutively with water (×2) and brine, dried and concentrated in vacuo to give a residue. This was purified by chromatography (50 g silica gel; 2% ether in petroleum ether as eluant) followed by distillation to give the title compound as an oil. b.p. 32° C./0.3 mmHg (Found: C, 40.67; H, 7.28; Br, 33.68. $C_8H_{17}OBrSi$ requires C, 40.51; H, 7.22; Br, 33.69%), δ (100 MHz) 0.13 (9H, s), 0.48 (2H, m), 0.77 (2H, m), 2.03, (2H, t, J 8), and 3.55 (2H, t, J 8).

PREPARATION 3

2-[1-(2-p-Toluenesulphonyloxyethyl)cyclopropyloxy]-tetrahydro-4H-pyran (Compound 4)

To a solution of 1-(2-p-toluenesulphonyloxyethyl)cyclopropanol (an intermediate in Preparation 2) (1.30 g) in dichloromethane (15 ml) at room temperature was added dihydropyran (0.88 g, 95%) and pyridinium p-toluenesulfonate (0.1 g). After 5 hours, the reaction solution was diluted with ether (70 ml) and extracted consecutively with water, 5% sodium hydrogen carbonate solution, and brine. After drying and removal of the solvent in vacuo, the product was purified by chromatography (50 g silica gel; 30% ether in petroleum ether as solvent) followed by recrystallisation from hexane to give the title compound as plates, m.p. 56°-57° C. (Found C, 59.99; H, 7.13; S 9.37. $C_{17}H_{24}O_5S$ requires C, 59.98; H, 7.11; S 9.42%), δ (100 MHz) 0.5 (2H, m), 0.85 (2H, m), 1.2-2.4 (8H, m), 3.1-3.9 (4H, m), 4.55 (1H, m), 7.6 (3H, m), 7.9 (2H, m).

PREPARATION 4

1-(2-Bromoethyl)cyclopentyloxytrimethylsilane (Compound 5)

Following the procedures in sequence described below (Preparation 5) for the synthesis of the cyclohexyl analogue (6) over four steps, the title compound was prepared analogously by using 1-(ethoxycarbonylmethyl)cyclopentanol as starting material instead of 1-(ethoxycarbonylmethyl)cyclohexanol.

PREPARATION 5

1-(2-Bromoethyl)cyclohexyloxytrimethylsilane (Compound 6)

1-(Ethoxycarboxylmethyl)cyclohexanol (14 g) was added dropwise over 1 hour to an ice-cooled, stirred suspension of lithium aluminium hydride (3.5 g) in dried ether (250 ml), and stirring was continued overnight at room temperature. After destruction of excess hydride by the careful addition of water to the ice-cooled mixture, the ether layer was separated, washed with brine and dried. Concentration in vacuo to constant weight gave 1-(2-hydroxyethyl)cyclohexanol [D (n=1, $R^1+R^2=-(CH_2)_5-$)] in sufficient purity for the next step. Distillation of a portion gave an analytical sample, b.p. 78°-79° C./0.2 mmHg (Found: C, 66.53; H, 11.13. $C_8H_{16}O_2$ requires C, 66.63; H, 11.18%).

To an ice-cooled solution of 1-(2-hydroxyethyl)cyclohexanol (11.2 g) and pyridine (17 ml) in dichloromethane (100 ml) was added p-toluenesulphonyl chloride (19.5 g). The mixture was then stirred at room temperature under an atomosphere of nitrogen for 3 hours before being partitioned between ether (300 ml) and water. The organic layer was washed consecutively with 4N hydrochloric acid, water, 5% sodium hydrogen carbonate solution, and brine, and dried. Concentration in vacuo gave a residue which was purified by chromatography (500 g silica gel; 20% ethyl acetate in petroleum ether as eluent) to give 1-(2-p-toluenesulphonyloxyethyl)cyclohexanol [E; n=1, $R^1+R^2=-(CH_2)_5-$] as an oil.

A stirred solution of lithium bromide (70 g) and 1-(2-p-toluenesulphonyloxyethyl)cyclohexanol (16.4 g) in acetone (350 ml) was heated under reflux for 1 hour. The cooled reaction mixture was partially concentrated in vacuo and then partitioned between ether (300 ml) and water. The ether phase was washed with water and brine, dried and concentrated in vacuo to give 1-(2-bromoethyl)cyclohexanol [H; n=1, $R^1+R^2=-(CH_2)_5-$] as an oil.

To an ice-cooled solution of 1-(2-bromoethyl)cyclohexanol (4.2 g), triethylamine (5.6 ml) and 4-dimethylaminopyridine (0.3 g) in dichloromethane (50 ml) stirred under a nitrogen atmosphere was added dropwise trimethylsilyl chloride (3.8 ml). After a further 40 minutes stirring on the ice bath, stirring was continued at room temperature for 16 hours. The reaction mixture was partitioned between ether (200 ml) and water. The organic layer was washed consecutively with water (×2) and brine, dried and concentrated in vacuo to give a residue. This was purified by chromatography (150 g silica gel; 2% ether in petroleum ether as eluant) followed by distillation to give the title compound as an oil. b.p. 85°-87° C./0.2 mmHg (Found: C, 47.44; H, 8.33; Br, 28.85. $C_{11}H_{23}OBrSi$ requires C, 47.30; H, 8.30; Br, 28.61%), δ (100 MHz) 0.13 (9H, s), 1.1-1.8 (10H, m), 2.05, (2H, m), and 3.4 (2H, m).

PREPARATION 6

1-(3-bromopropyl)cyclopropyloxytrimethylsilane (Compound 7)

Following the procedures in the sequence described above for the synthesis of the 2-bromoethyl analogue (3) over six steps (Preparations 1 and 2), the title compound was prepared analogously by using 3-acetyl-1-propanol as starting material instead of 4-hydroxy-2-butanone.

PREPARATION 7

6-Bromo-2-methyl-2-trimethylsilyloxyhexane (Compound 8)

To a stirred, ice-cooled solution of ethyl 5-bromopentanoate (G, n=3) (18.7 ml) in dried ether (100 ml) was added dropwise over 1 hour a filtered solution of Grignard reagent, prepared from magnesium (10 g) and methyl iodide (25 ml) in dried ether (200 ml). After a further 30 minutes on the ice bath, the reaction mixture was allowed to warm to room temperature over 30 minutes before being poured onto a stirred, ice-cooled solution of ammonium chloride (30 g) in water (200 ml). After the vigorous reaction had subsided, the ether layer was separated, and the aqueous layer was extracted with more ether. The combined ether layers were washed consecutively with water and brine, dried, and concentrated in vacuo to give the crude intermediate carbinol H (n=3, $R^1=R^2=Me$) as a pale yellow oil. This was dissolved in dichloromethane (130 ml) and triethylamine (40 ml) and 4-dimethylaminopyridine (0.2 g) added. The stirred solution was ice-cooled during the addition of trimethylsilyl chloride (27 ml) dropwise over 30 minutes. The reaction mixture was then stirred at room temperature for 2 hours before being partitioned between ether (500 ml) and water (500 ml). The ether layer was washed four times with water, once with brine, and dried. After removing the solvent in vacuo, the residue was distilled to give a product, b.p. 103°–105° C./11 mmHg. A portion (5 g) of the product was purified by chromatography (150 g silica gel; 1% ether in petroleum ether as eluant) and redistilled to give the pure bromide (8) as an oil, δ (300 MHz) 0.10 (9H, s), 1.21 (6H, s), 1.45 (4H, m), 1.86 (2H, m) and 3.42 (2H, t, J 7).

PREPARATION 8

7-Bromo-3-ethyl-3-trimethylsilyloxyheptane (Compound 9)

The compound was prepared according to the procedure described in Preparation 7, except that the Grignard reagent was prepared from ethyl bromide (45 g), via the intermediate carbinol H (n=3, $R^1=R^2=Et$). 9; B.p. 88° C./0.5 mmHg; δ (300 MHz) 0.09 (9H, s), 0.81 (6H, t), 1.30–1.55 (8H, m), 1.84 (2H, m) and 3.41 (2H, t, J 7).

PREPARATION 9

7-Bromo-2-methyl-2-trimethysilyloxyheptane (Compound 10)

The compound was prepared according to the procedure described in Preparation 7, except that the ethyl 5-bromopentanoate was substituted with ethyl 6-bromohexanoate (G, n=4) (26 g), via the intermediate carbinol H (n=4, $R^1=R^2=Me$). The oily bromide (10) had b.p. 87°–88° C./1 mmHg and δ (300 MHz) 0.10 (9H, s), 1.20 (6H, s), 1.41 (6H, m), 1.89 (2H, m) and 3.41 (2H, t, J 7).

PREPARATION 10

8-Bromo-3-methyl-2-trimethylsilyloxyoctane (Compound 11)

The compound was prepared according to the procedure described in Preparation 7, except that the ethyl 5-bromopentanoate was substituted with ethyl 7-bromoheptanoate (G, n=5) (28 g), via the intermediate carbinol H (n=5, $R^1=R^2=Me$).

PREPARATION 11

2-[1-(2-Phenylsulphonylethyl)cyclopropyloxy]tetrahydro-4H-pyran (Compound 12)

2-[1-(2-p-Toluenesulphonyloxyethyl)cyclopropyloxy]tetrahydro-4H-pyran (Compound 4) (1.30 g) was dissolved in a premixed, stirred solution of potassium tert-butoxide (0.45 g) and thiophenol (0.50 g) in N,N-dimethylformamide (10 ml) at room temperature. After a few minutes a precipitate started forming, and after 30 minutes the mixture was partitioned between ether (50 ml) and water. The organic layer was washed consecutively with 2N sodium hydroxide solution, water, and brine. Drying and concentration in vacuo gave a residue which was purified by chromatography (50 g silica gel; 10% ether in petroleum ether as eluant) to give 2-[1-(2-phenylthioethyl)cyclopropyloxy]tetrahydro-4H-pyran. Distillation of a portion gave an analytical sample, b.p. 121°–122° C./0.1 mmHg. (Found: C, 69.07; H, 8.01; S, 11.31. $C_{16}H_{22}O_2S$ requires C, 69.03; H, 7.97; S, 11.52%).

To a stirred solution of 2-[1-(2-phenylthioethyl)cyclopropyloxy]tetrahydro-4H-pyran (0.43 g) in methanol (5 ml) was added sodium hydrogen carbonate (0.3 g), aqueous sodium tungstate solution (2%, 0.3 ml) and hydrogen peroxide (100 vol, 0.4 g). The reaction mixture was stirred at 50° C. for 2 hours and then cooled and partitioned between dichloromethane (50 ml) and water. The organic layer was washed with brine, dried, and concentrated in vacuo. The crude product so obtained was distilled to give the title compound as a viscous oil, b.p. 176°–177° C./0.15 mmHg. (Found: C, 61.86; H, 7.19; S, 10.27. $C_{16}H_{22}O_4S$ requires C, 61.91; H, 7.14; S, 10.33%), δ (100 MHz) 0.5 (2H, m), 0.85 (2H, m), 1.2–2.4 (8H, m), 3.1–3.9 (4H, m), 4.55 (1H, m), 7.6 (3H, m), 7.9 (2H, m).

PREPARATION 12

6-Hydroxy-6-methylheptyl phenyl sulphone (Compound 13)

To a solution of 7-bromo-2-methyl-2-trimethylsilyloxyheptane (10) (14.0 g) in methanol (55 ml) at room temperature was added ethanolic hydrogen chloride (ca. 1M, 0.2 ml). After 10 minutes the solution was concentrated in vacuo (at room temperature) to constant weight. The residue was taken up in chloroform and reconcentrated to constant weight to give 7-bromo-2-methyl-2-heptanol (H, n=4, $R^1=R^2=Me$) as a chromatographically homogenous oil. The product was dissolved in THF (10 ml) and added to a premixed, stirred solution of potassium tert-butoxide (6.7 g) and thiophenol (3.6 ml) in N,N-dimethylformamide (50 ml) at room temperature. After a few minutes a precipitate started forming, and after 30 minutes the mixture was partitioned between ethyl acetate (300 ml) and water (200 ml). The organic layer was washed consecutively with 2N sodium hydroxide solution, water and brine. Drying and concentration in vacuo gave 6-hydroxy-6-methylheptyl phenyl sulphide as a chromatographically homogenous oil. This was dissolved in methanol (60 ml), and to the stirred solution was added sodium hydrogen carbonate (4.7 g), aqueous sodium tungstate solution (2%, 5 ml) and hydrogen peroxide (100 vol, 11.8 ml). The initial exothermic reaction which ensued was checked by momentary ice-cooling. The reaction mixture was then stirred at 50° C. for 1 hour. After cooling, the mixture was partitioned between dichloromethane (200 ml) and water. The aqueous layer was extracted with more dichloromethane, and the combined dichloromethane layers were washed with water, brine, and dried. Concentration in vacuo gave a crude product which was purified by chromatography (150 g silica gel; ether as eluant) to give the sulphone (13) as a viscous oil, $\delta$ (300 MHz) 1.18 (6H, s), 1.4 (7H, m), 1.75 (2H, m), 3.09 (2H, m), 7.5–7.75 (3H, m), 7.90 (2H, m).

PREPARATION 13

6-Hydroxy-6-methylheptyldiphenyl-phosphine oxide (Compound 14)

A solution of 7-bromo-2-methyl-2-trimethylsilyloxyheptane (10) (1.7 g) in dry THF (2 ml) was added to a solution of lithium diphenylphosphide [prepared by treating diphenylphosphine (1.0 ml) in dry THF (5 ml) at 0° C. under nitrogen with n-butyl-lithium (1.4M in hexanes, 4 ml)] at −70° C. dropwise over 5 minutes (syringe). The pale yellow solution was diluted with petroleum ether (100 ml) and extracted with water and brine, and dried. Concentration in vacuo gave an oil (crude 6-methyl-6-trimethylsilyloxyheptyldiphenylphosphine) which was dissolved in dichloromethane (30 ml) and shaken with hydrogen peroxide solution (6%, 50 ml) for 5 minutes. The aqueous phase was separated from the organic phase, and extracted with more dichloromethane. The combined organic phases were washed with brine, dried and concentrated in vacuo to give an oil (crude 6-methyl-6-trimethylsilyloxyheptyldiphenylphosphine oxide). This was dissolved in dichloromethane (5 ml) and methanol (30 ml) containing a trace of hydrogen chloride. After 10 minutes, the solution was concentrated in vacuo to give an oil. This was crystallized from ether to give the phosphine oxide (14) as needles, $\delta$ (300 MHz) 1.17 (6H, s), 1.30–1.50 (6H, m), 1.50–1.75 (3H, m), 2.26 (2H, m), 7.40–7.55 (6H, m), 7.65–7.80 (4H, m).

PREPARATION 14

Compounds 20

A stirred solution of the seleno-acetal (1) (0.75 g) in dried THF (5 ml) was cooled to −70° C. under nitrogen and treated dropwise via a syringe with n-butyl-lithium solution (1.5M i hexane, 0.7 ml). After 10 minutes, compound 3 (0.36 g) was added dropwise, and after a further 10 minutes, at −70° C. the cooling bath was removed and the reaction solution allowed to warm to room temperature. Two hours later, the reaction solution was diluted with ether (50 ml) and extracted with water and brine. The ether layer was dried and concentrated in vacuo to give a residue which was purified by chromatography (100 g silica gel; 2% ether in petroleum ether as eluant) to give compound 20a (less polar isomer), $\delta$ (100 MHz) 0.06 (12H, s), 0.15 (9H, s), 0.56 (3H, s), 0.87 (9H, s), 0.90 (9H, s), 1.05 (3H, d, J 6), 1.95 (3H, s), 4.2 (1H, m), 4.5 (1H, m), 4.9 (2H, m), 5.8 (1H, d, J 11), 6,45 (1H, d, J 11); $\lambda_{max}$ 270 nm, and compound 20b (more polar isomer), $\delta$ (100 MHz) 0.06 (12H, s), 0.14 (9H, s), 0.57 (3H, s), 0.87 (9H, s), 0.90 (9H, s), 0.25–0.8 (4H, m), 0.95 (3H, m), 1.96 (3H, s), 4.2 (1H, m), 4.5 (1H, m), 4.9 (2H, bs), 5.8 (1H, d, J 11), 6.45 (1H, d, J 11); $\lambda_{max}$ 270 nm.

PREPARATION 15

Compound 21

To a stirred ice-cooled solution of compound 20a (0.20 g) in dried THF (5 ml) was added a solution of tetra-n-butylammonium fluoride trihydrate (0.15 g) in THF (1 ml). After stirring for a further 10 minutes, the reaction solution was partitioned between ethyl acetate (40 ml) and 2% sodium hydrogen carbonate solution (30 ml), and the organic layer was washed with water and brine, dried and concentrated. The residue was purified by chromatography (30 g silica gel, 20% ether in petroleum ether as eluant) to give compound 21a as needles (from ether-methanol), $\delta$ (100 MHz) 0.06 (12H, s), 0.56 (3H, s), 0.4–0.8 (4H, m), 0.87 (9H, s), 0.90 (9H, s), 1.05 (3H, d, J 6), 1.96 (3H, s), 4.2 (1H, m), 4.5 (1H, m), 4.95 (2H, m), 5.8 (1H, d, J 11), 6.45 (1H, d, J 11); $\lambda_{max}$ 270 nm.

Similar treatment of compound 20b gave compound 21b (more polar isomer) as needles (from ether-methanol), $\delta$ (100 MHz) 0.06 (12H, s), 0.57 (3H, s), 0.4–0.85 (4H, m), 0.87 (9H, s), 0.90 (9H, s), 0.95 (3H, m), 1.98 (3H, s), 4.2 (1H, m), 4.5 (1H, m), 4.95 (2H, m), 5.8 (1H, d, J 11), 6.45 (1H, d, J 11); $\lambda_{max}$ 270 nm.

PREPARATION 16

Compound 22

To a solution of compound 21a (0.20 g) in dichloromethane (8 ml) at room temperature was added dihydropyran (95%, 0.5 g) and pyridinium p-toluenesulfonate (25 mg). After 1 hour, the reaction solution was diluted with ether (70 ml) and extracted consecutively with water, 5% sodium hydrogen carbonate solution, and brine. After drying and removal of the solvent in vacuo, the product was purified by chromatography (30 g silica gel; 5% ether in petroleum ether as eluant) to give 22 as needles (from ether-methanol), $\delta$ (100 MHz) 0.06 (12H, s), 0.56 (3H, s), 0.87 (9H, s), 0.90 (9H, s), 1.05 (3H, d, J 6), 1.95 (3H, s), 3.5 (1H, m), 3.9 (1H, m), 4.2 (1H, m), 4.5 (1H, m), 4.75 (1H, bs), 4.9 (2H, m), 5.8 (1H, d, J 11), 6.45 (1H, d, J 11); $\lambda_{max}$ 270 nm.

PREPARATION 17

Compound 23

Compound 22 (75 mg) was dissolved in ether (0.5 ml), and liquid sulphur dioxide (2 ml) (with cooling) added. The sulphur dioxide was allowed to boil under reflux for 1 hour, and then the solvent was removed in vacuo to give a diastereoisomeric mixture of sulphur dioxide adducts (cf. Tetrahedron Letters, 1987, 28, 1337) of compound 22. The product (in a Pyrex flask) was dissolved in toluene (3 ml) and tri-n-butylstannane (0.2 g) added. A nitrogen atmosphere was established, and the reaction flask was water cooled (20° C.) during illumination with radiation from a high pressure Hg lamp (type: Hanau TQ 718Z2) for 1 hour. The solution was then concentrated in vacuo to give a residue which was purified by chromatography (15 g silica gel; 20% ether in petroleum ether as eluant). First eluted was the major (6S) sulphur dioxide adduct of compound 23. This was followed by the minor (6R) diastereoisomer. Fractions containing the two isomers were combined (each gives the same product in the next step, though a pure sample of each isomer was isolated for characterization purposes) and concentrated to give an oil. This was dissolved or suspended together with sodium hydrogen carbonate (50 mg) in 96% ethanol (3 ml) and the stirred mixture was heated under reflux under a nitrogen atmosphere for 90 minutes. After cooling, the reaction solution was partitioned between ethyl acetate (20 ml) and water, and the ethyl acetate layer was washed with brine and dried. Removal of the solvent in vacuo gave a product which was purified by chromatography (15 g silica gel; 10% ether in petroleum ether as eluant) to give 23, $\lambda_{max}$ 270 nm.

PROCEDURE 1

Preparation of Compound III ($R^3=R^4=H$) from Seleno-acetal (1) and Side Chain Fragment A.

A stirred solution of the seleno-acetal (1) (0.75 g) in dried THF (5 ml) was cooled to $-70°$ C. under nitrogen and treated dropwise via a syringe with n-butyl-lithium solution (1.5M i hexane, 0.7 ml). After 10 minutes, the side chain fragment A was added dropwise, and after a further 10 minutes, at $-70°$ C. the cooling bath was removed and the reaction solution allowed to warm to room temperature. Two hours later, the reaction solution was diluted with ether (50 ml) and extracted with water and brine. The ether layer was dried and concentrated in vacuo to give a crude oil containing compound II ($R^6=H$, $R^7=SeMe$) as a mixture of diastereoisomers at C-22. This was dissolved in ether (2 ml), and liquid sulphur dioxide (15 ml) (with cooling) and water (0.2 ml) added. The sulphur dioxide was allowed to boil under reflux for 1 hour, and then the solvent was removed in vacuo to give a diastereoisomeric mixture of sulphur dioxide adducts (cf. Tetrahedron Letters, 1987, 28, 1337) of the compound II ($R^6=H$, $R^7=SeMe$). The product (in a Pyrex flask) was dissolved in toluene (20 ml) and tri-n-butylstannane (2 g) added. A nitrogen atmosphere was established, and the reaction flask was water cooled (20° C.) during illumination with radiation from a high pressure Hg lamp (type: Hanau TQ 718Z2) for 2 hours. The solution was then concentrated in vacuo to give a residue which was purified by chromatography (150 g silica gel; 40% ether in petroleum ether as eluant). First eluted was the major (6S) sulphur dioxide adduct of the compound III ($R^3=R^4=H$). This was followed by the minor (6R) diastereoisomer. Fractions containing the two isomers were combined (each gives the same product in the next step, though a pure sample of each isomer was isolated for characterization purposes) and concentrated to give an oil. This was dissolved or suspended together with sodium hydrogen carbonate (0.4 g) in 96% ethanol (10 ml) and the stirred mixture was heated under reflux under a nitrogen atmosphere for 90 minutes. After cooling, the reaction solution was partitioned between ethyl acetate (50 ml) and water, and the ethyl acetate layer was washed with brine and dried. Removal of the solvent in vacuo gave a product which was purified by chromatography (30 g silica gel; 30% ether in petroleum ether as eluant) to give III ($R^3=R^4=H$).

It should be noted that in Preparations 18, 19, 20, 34, 35, 36, 38, 39, and 46 the meaning of $R^5$ in the intermediates changes from $R^5=SiMe_3$ in II to $R^5=H$ after the treatment with sulphur dioxide.

PREPARATION 18

Compound 24

The compound was prepared using Procedure 1 in which the side chain fragment A was compound 6 (0.42 g); 24 δ (100 MHz) 0.06 (12H, s), 0.54 (3H, s), 0.87 (9H, s), 0.90 (9H, s), 4.2 (1H, m), 4.5 (1H, m), 4.9 (2H, m), 5.8 (1H, d, J 11), 6.45 (1H, d, J 11); $\lambda_{max}$ 270 nm.

PREPARATION 19

Compound 25

The compound was prepared using Procedure 1 in which the side chain fragment A was compound 8 (0.40 g). 25; δ (300 MHz) 0.05 (12H, s), 0.53 (3H, s), 0.85 (9H, s), 0.89 (9H, s), 0.91 (3H, d, J 6), 1.0–2.1 (31H, m, including 1.20 (6H, s)), 2.30 (1H, bd, J 14), 2.56 (1H, dd, J 14 and 5), 2.86 (1H, bd, J 11), 4.21 (1H, m), 4.53 (1H, m), 4.93 (1H, bs), 4.98 (1H, bs,), 5.81 (1H, d, J 11), 6.45 (1H, d, J 11); $\lambda_{max}$ 270 nm.

PREPARATION 20

Compound 26

The compound was prepared using Procedure 1 in which the side chain fragment A was compound 10 (0.42 g). 26; δ (300 MHz) 0.05 (12H, s), 0.53 (3H, s), 0.85 (9H, s), 0.89 (9H, s), 0.9 (3H, m), 0.95–2.05 (33H, m, including 1.20 (6H, s)), 2.29 (1H, bd, J 14), 2.55 (1H, dd, J 14 and 5), 2.86 (1H, bd, J 12), 4.20 (1H, m), 4.52 (1H, m), 4.93 (1H, bs), 4.97 (1H, bs,), 5.81 (1H, d, J 11), 6.45 (1H, d, J 11); $\lambda_{max}$ 270 nm.

PROCEDURE 2

Preparation of Compounds III [$R^3+R^4$=bond (22E)] from Aldehyde (2) and Side Chain Fragment B A solution of lithium di-iso-propylamide (0.4M in THF-hexanes, 3:1) was added dropwise via a syringe (10 minutes) to a solution of the side chain fragment B in dry THF (8 ml), stirred at $-25°$ C. under nitrogen. The resulting yellow solution was then cooled to $-40°$ C., and a solution of the aldehyde (2) (1.21 g) in dry THF (8 ml) was added dropwise (5 minutes). After stirring for 30 minutes, the reaction mixture was treated with ether (10 ml) and water (1 ml) and partitioned between ethyl acetate (100 ml) and water (50 ml). The organic layer was washed with brine, dried, and concentrated in vacuo to give a crude oil containing compound II ($R^6=S(O_2)Ph$, $R^7=OH$) as a mixture of diastereoisomers at C-22 and C-23. This was dissolved in ethyl acetate (5 ml) and diluted with methanol (50 ml, saturated with and containing suspended disodium hydrogen phosphate). To the ice-cooled mixture was added sodium amalgam (ca. 5% Na, 15 g), and the reaction mixture was stirred at 5° C. under nitrogen for 15 hours. The mixture was then partitioned between ethyl acetate (200 ml) and water (200 ml) (decanting from the mercury), and the organic layer was washed with brine, dried and concentrated in vacuo. Purification of the residue by chromatography gave III ($R^3+R^4$=bond (22E)).

PREPARATION 21

Compound 27

This compound was prepared using Procedure 2 in which the side chain fragment B was compound 13 (0.66 g) and 12 ml of the lithium di-iso-propylamide solution was used. The intermediate II has $R^5=OH$. The chromatography was performed on 150 g silica gel using 10% ethyl acetate in petroleum ether as eluant. 27; δ (300 MHz) 0.06 (12H, s), 0.54 (3H, s), 0.86 (9H, s), 0.90 (9H, s), 1.00 (3H, d, J 7), 1.15–2.1 (29H, m, including 1.20 (6H, s)), 2.30 (1H, bd, J 14), 2.55 (1H, dd, J, 14 and 5), 2.86 (1H, bd, J 12), 4.21 (1H, m), 4.53 (1H, m), 4.93

(1H, bs), 4.98 (1H, bs), 5.26 (2H, m), 5.81 (1H, d, J 11), and 6.45 (1H, d, J 11); $\lambda_{max}$ 270 nm.

PROCEDURE 3

Preparation of Compound IV from the Corresponding Compound III

A mixture of anthracene (0.10 g), triethylamine (20 mg), and the compound III (0.20 g) in toluene (15 ml), stirred under an atmosphere of nitrogen in a Pyrex flask immersed in a water bath at 20° C., was illuminated with radiation from a high pressure Hg lamp (type: Hanau TQ 718Z2) for 30 minutes. The reaction mixture was filtered and concentrated in vacuo to give a residue. This was purified by chromatography (30 g silica gel; 30% ether in petroleum ether as eluant) to give IV.

PREPARATION 22

Compound 28

The compound was prepared using Procedure 3 in which starting material III was compound 23. In this preparation, the eluant used was 5% ether in petroleum ether. 28; $\lambda_{max}$ 265 nm.

PREPARATION 23

Compound 29

The compound was prepared using Procedure 3 in which starting material III was compound 24. 29; δ (300 MHz) 0.06 (12H, s), 0.53 (3H, s), 0.88 (18H, s), 0.92 (3H, d, J 6), 1–2.05 (31H, m), 2,21 (1H, dd, J 13 and 7), 2.45 (1H, dd, J 13 and 3), 2.82 (1H, bd, J 12), 4.19 (1H, m), 4.38 (1H, m), 4.87 (1H, d, J 2), 5.18 (1H, m), 6.02 (1H, d, J 11), 6.24 (1H, d, J 11); $\lambda_{max}$ 265 nm.

PREPARATION 24

Compound 30

The compound was prepared using Procedure 3 in which starting material III was compound 25. 30; δ (300 MHz) 0.05 (12H, s), 0.52 (3H, s), 0.87 (18H, s), 0.91 (3H, m), 0.95–2.05 (31H, m, including 1.20 (6H, s)), 2.20 (1H, dd, J 13 and 7), 2.44 (1H, dd, J 13 and 4), 2.81 (1H, bd, J 12), 4.18 (1H, m), 4.36 (1H, m), 4.86 (1H, d, J 2), 5.17 (1H, m), 6.01 (1H, d, J 11), 6.23 (1H, d, J 11); $\lambda_{max}$ 265 nm.

PREPARATION 25

Compound 31

The compound was prepared using Procedure 3 in which starting material III was compound 26. 31; δ (300 MHz) 0.05 (12H, s), 0.52 (3H, s), 0.87 (18H, s), 0.9 (3H, m), 0.9–2.05 (33H, m, including 1.20 (6H, s)), 2.21 (1H, dd, J 13 and 7), 2.44 (1H, dd, J 13 and 4), 2.81 (1H, bd, J 11), 4.18 (1H, m), 4.36 (1H, m), 4.86 (1H, d, J 2), 5.17 (1H, m), 6.01 (1H, d, J 11), 6.23 (1H, d, J 11); $\lambda_{max}$ 265 nm.

PREPARATION 26

Compound 32

The compound was prepared using Procedure 3 in which starting material III was compound 27. 32; δ(300 MHz) 0.06 (12H, s), 0.53 (3H, s), 0.87 (18H, s), 1.0 (3H, d, J 7), 1.1–2.1 (29H, m, including 1.20 (6H, s)), 2.2 (1H, dd, J 13 and 7), 2.45 (1H, dd, J 13 and 4), 2.81 (1H, bd, J 11), 4.2 (1H, m), 4.35 (1H, m), 4.85 (1H, m), 5.2 (3H, m), 6.01 (1H, d, J 11), 6.23 (1H, d, J 11); $\lambda_{max}$ 265 nm.

PREPARATION 27

1,3,(R)-Decanediol [D (n=1, $R^1$=H, $R^2$=Hep)]

A solution of ethyl 3-oxodecanoate (25.7 g) in ethanol (360 ml) and aqueous potassium hydroxide (260 ml, 1M) was stirred at room temperature for 18 hours. The solvent was removed in vacuo to give crude potassium 3-oxodecanoate.

Baker's yeast (Saccharomyces cerevisiae, Malteserkors®, De danske Spritfabrikker, 640 g), D-glucose (720 g), potassium dihydrogenphosphate (1.6 g) and magnesium sulfate (0.8 g) in water (2 l) were stirred at room temperature for 30 minutes. A solution of the above potassium 3-oxodecanoate in water (1.5 l) was added. The mixture was stirred at ambient temperature and pH was kept between 6.0 and 6.5 by automatic titration with 1M potassium hydroxide or 1M citric acid. After 48 hours Celite® was added, and after stirring for 30 minutes more the mixture was filtered. The filtrate was acidified to pH 2.5 with concentrated hydrochloric acid, extracted with methylene chloride (2×2 l), dried and evaporated in vacuo to give crude 3(R)-hydroxydecanoic acid.

The crude 3-hydroxydecanoic acid (12 g) was dissolved in ether (100 ml) and diazomethane (0.15 mol) in ether (approx. 100 ml) was added slowly.

Excess diazomethane was destroyed with acetic acid (2 ml). The reaction mixture was washed with saturated sodium hydrogencarbonate, dried and evaporated in vacuo. The residue was purified by chromatography (silica gel, 180 g, ether/pentane 1:2 as eluent) to give methyl 3(R)-hydroxy-decanoate as an oil. δ (300 MHz) 0.88 (3H, t), 1.15–1.60 (12H), 2.42 (1H, dd, J 16 and 9), 2.53 (1H, dd, J 16 and 3), 3.71 (3H, s) and 4.01 (1H, m).

Optical purity (>98% e.e.) was determined by $^1$HNMR chiral shift reagent studies (cf. M. Hirama, M. Shimizu and M. Iwashita, Chem. Commun. 1983 599–600).

A solution of methyl 3(R)-decanoate (3.5 g) in dry ether (15 ml) was slowly added to a suspension of lithium aluminiumhydride (0.50 g) in dry ether (25 ml), and the mixture was stirred at room temperature for 40 minutes. Excess hydride was destroyed by dropwise addition of water (5 ml). After centrifugation the precipitate was extracted with ethyl acetate (3×40 ml). The combined organic solutions were washed with water (50 ml), dried and evaporated to dryness in vacuo to yield the title compound as an oil. δ (300 MHz) 0.88 (3H, t), 1.15–1.60 (12H, m), 1.71 (2H, m), 2.30–2.55 (2H, m) and 3.87 (3H, m).

PREPARATION 28

1-Iodo-3(R)-trimethylsilyloxydecane (Compound 16)

A solution of 1,3(R)-decandiol (2.5 g) in pyridine (20 ml) was cooled to −20° C., and 4-toluenesulfonyl chloride (3.0 g) in pyridine (20 ml) was added over 20 minutes. After stirring for 30 minutes, water (4 ml) was added, followed by methylene chloride (30 ml). The mixture was washed with hydrochloric acid (1M, 2×50 ml) and sodium hydroxide solution (1M, 50 ml), dried and evaporated in vacuo. The residue (crude 1-(4-toluenesulfonyloxy)-3(R)-decanol) was refluxed with sodium iodide (9 g) in acetone (110 ml) for 1.5 hour. After cooling, the mixture was filtered and the filtrate evaporated to dryness in vacuo. The residue was dissolved in methylene chloride (100 ml), washed with water (100 ml) and sodium hydroxide solution (1M, 100 ml), dried and evaporated. Chromatography (silica gel, 60 g, methylene chloride/ethyl acetate 20:1 as eluent) gave 1-iodo-3(R)-decanol as an oil, δ (300 MHz) 0.89 (3H, t), 1.15–1.60 (13H, m), 1.92 (2H, m), 3.32 (2H, m) and 3.72 (1H, m).

To a solution of 1-iodo-3(R)-decanol (490 mg) in methylene chloride (10 ml) was added trimethylsilyl chloride (336 mg) and N-ethyldiisopropylamin (398 mg). After stirring for 1 hour, the mixture was washed with phosphate buffer (pH 6.5, 0.066M, 10 ml) and brine (10 ml), dried and evaporated in vacuo. The residue was purified by chromatography (silica gel, 20 g, methylene chloride as eluent) to give the title compound as an oil, δ (300 MHz) 0.13 (9H, s), 0.87 (3H, t), 1.15–1.50 (12H, m), 1.92 (2H, m), 3.21 (2H, m) and 3.70 (1H, m).

PREPARATION 29

1-Iodo-3(S)-trimethylsilyloxybutane (Compound 15a)

1-Iodo-3(S)-butanol was prepared using the method described in Preparation 28, but replacing 1,3(R)-decanediol with 1,3(S)-butanediol. The intermediate 1-iodo-3(S)-butanol was purified by distillation, b.p. 52°–54° C./0.5 mmHg; δ (300 MHz) 1.24 (3H, d, J 6), 1.60 (1H, bd), 1.97 (2H, m), 3.29 (2H, t, J 7) and 3.93 (1H, m). 15a; δ (300 MHz) 0.14 (9H, s), 1.17 (3H, d, J 6), 1.93 (2H, m), 3.22 (2H, m) and 3.87 (1H, m).

PREPARATION 30

1-Iodo-3(R)-trimethylsilyloxybutane (Compound 15b)

The title compound was prepared using the method described in Preparation 28, but replacing 1,3(R)-decanediol with 1,3(R)-butanediol. 15b; δ (300 MHz) 0.14 (9H, s), 1.17 (3H, d, J 6), 1.93 (2H, m), 3.22 (2H, m) and 3.87 (1H, m).

PREPARATION 31

6-Bromo-3-ethyl-3-trimethylsilyloxyhexane (Compound 17)

The compound was prepared according to the procedure described in Preparation 7, except that the Grignard reagent was prepared from the ethylbromide (45 g) and the ethyl 5-bromopentanoate was substituted with ethyl 4-bromobutyrate (G, n=2) (23 g), via the intermediate carbinol H (n=2, $R^1=R^2=Et$). The oily bromide (17) had b.p. 52°–53° C./0.1 mmHg; δ (300 MHz) 0.09 (9H, s), 0.82 (6H, t, J 7), 1.50 (6H, m), 1.85 (2H, m) and 3.40 (2H, t, J 7).

PREPARATION 32

8-Bromo-4-propyl-4-trimethylsilyloxy octane (Compound 18)

The compound was prepared according to the procedure described in Preparation 7, except that the Grignard reagent was prepared from propylbromide (51 g), via the intermediate carbinol H (n=3, $R^1=R^2=Pr$). The oily bromide (18) had b.p. 102° C/0.5 mmHg; δ (300 MHz) 0.08 (9H, s), 0.88 (6H, t, J 7), 1.15–1.50 (12H, m), 1.84 (2H, m) and 3.41 (2H, t, J 7).

PREPARATION 33

5-Hydroxy-5-methylhexyl phenylsulphone (Compound 19)

The compound was prepared using the procedure of Preparation 12, except using 6-bromo-2-methyl-2-trimethylsilyloxyhexane (compound 8) as starting material, via the corresponding intermediates 6-bromo-2-methyl-2-hexanol (H, n=3, $R^1=R^1=$ Me) and 5-hydroxy-5-methylhexyl phenyl sulphide. 19; δ (300 MHz) 1.17 (6H, s), 1.42 (4H, m), 1.59 (1H, bs), 1.72 (2H, m), 3.11 (2H, m), 7.5–7.7 (3H, m) and 7.90 (2H, m).

PREPARATION 34

Compound 39

The compound was prepared using Procedure 1 in which the side chain fragment A was composed 15a (0.44 g). 39; δ (300 MHz) 0.06 (12H, s), 0.53 (3H, s), 0.85 (9H, s), 0.89 (9H, s), 0.92 (3H, d, J 7), 1.00–2.10 [24H, m, including 1.18 (3H, d, J=6)], 2.30 (1H, bd), 2.55 (1H, dd, J 14 and 6), 2.86 (1H, bd), 3.79 (1H, m), 4.21 (1H, m), 4.53 (1H, m), 4.93 (1H, m), 4.98 (1H, m), 5.81 (1H, d, J 11) and 6.45 (1H, d, J 11).

PREPARATION 35

Compound 40

The compound was prepared using Procedure 1 in which the side chain fragment A was compound 15b (0.44 g). 40 δ (300 MHz) 0.06 (12H, s), 0.53 (3H, s), 0.85 (9H, s), 0.89 (9H, s), 0.92 (3H, d, J 7), 1.00–2.10 [24H, m, including (3H, d, J=6)], 2.30 (1H, bd), 2.55 (1H, dd, J 14 and 6), 2.86 (1H, bd), 3.79 (1H, m), 4.21 (1H, m), 4.53 (1H, m), 4.93 (1H, m), 4.98 (1H,m), 5.81 (1H, d, J 11) and 6.45 (1H,

PREPARATION 36

Compound 41

The compound was prepared using Procedure 1 in which the side chain fragment A was compound 16 (0.57 g). 41 δ (300 MHz) 0.06 (12H, m), 0.53 (3H, s), 0.60–2.10 [57H, m, including 0.85 (9H, s), 0.89 (9H, m)], 2.30 (1H, m), 2.56 (1H, m), 2.86 (1H, m), 3.58 (1H, m), 4.21 (1H, m), 4.52 (1H, m), 4.93 (1H, m), 4.98 (1H, m), 5.81 (1H, d, J 11) and 6.45 (1H, d. J 11).

PREPARATION 37

Compound 42

This compound was prepared using Procedure 2 in which the side chain fragment B was compound 19 (0.63 g), and 12 ml of the lithium di-iso-propylamide solution was used. The following modification was employed: Before the addition of ether and water to the reaction mixture, benzoyl chloride (0.6 ml) was added dropwise, and the mixture was allowed to warm to 0° C. and was stirred at this temperature for 30 minutes. The compound II has $R^6=S(O_2)Ph$ and $R^7=OC(O)Ph$, and $R^5=OH$. The chromatography of III was performed on 150 g silica gel using 40% ether in petroleum ether as eluant. 42; δ (300 MHz) 0.06 (12H, s), 0.54 (3H, s), 0.86 (9H, s), 0.90 (9H, s), 1.00 (3H, d, J 7), 1.15–2.1 (27H, m, including 1.20 (6H, s)), 2.30 (1H, bd, J 14), 2.55 (1H, dd, J 14 and 5), 2.86 (1H, bd, J 12), 4.21 (1H, m), 4.53 (1H, m), 4.93 (1H, bs), 4.98 (1H, bs), 5.28 (2H, m), 5.81 (1H, d, J 11), and 6.45 (1H, d, J 11); $\lambda_{max}$ 270 nm.

PREPARATION 38

Compound 43

The compound was prepared using Procedure 1 in which the side chain fragment A was compound 9 (0.47 g). In this preparation the eluant used in the final chromatography was 20% ether in petroleum ether 43; δ (300 MHz) 0.06 (12H, m), 0.53 (3H, s), 0.60–2.10 [56H, m, including 0.86 (9H, s), and 0.89 (9H, s)], 2.30 (1H, m), 2.55 (1H, m), 2.86 (1H, m), 4.21 (1H, m), 4.53 (1H, m), 4.93 (1H, m), 4.98 (1H, m), 5.82 (1H, d, J 11), and 6.45 (1H, d, J 11).

PREPARATION 39

Compound 44

The compound was prepared using Procedure 1 in which the side chain fragment A was compound 18 (0.56 g). In this preparation the eluant used in the final chromatography was 15% ether in petroleum ether 44; $\delta$ (300 MHz) 0.05 (12H, m), 0.53 (3H, s), 0.60–2.10 [60H, s, including 0.86 (9H, s) and 0.89 (9H, s)], 2.30 (1H, m), 2.55 (1H, m), 2.86 (1H, m), 4.21 (1H, m), 4.52 (1H, m), 4.93 (1H, m), 4.98 (1H, m), 5.81 (2H, d, J 11), and 6.45 (1H, d, J 11).

PREPARATION 40

Compound 45

The compound was prepared using procedure 3 in which starting material III was compound 39. 45; $\delta$(300 MHz) 0.06 (12H, s), 0.52 (3H, s), 0.70–2.10 [45H, m, including 0.87 (18H, s), 1.18 (3H, d, J 6)], 2.20 (1H, m), 2.44 (1H, m), 2.81 (1H, m), 3.79 (1H, m), 4.18 (1H, m), 4.36 (1H, m), 4.86 (1H, m), 5.17 (1H, m), 6.00 (1H, d, J 11), and 6.23 (1H, d, J 11); $\lambda_{max}$ 265 nm.

PREPARATION 41

Compound 46

The compound was prepared using Procedure 3 in which starting material III was compound 40. 46; $\delta$ (300 MHz) 0.06 (12H, s), 0.52 (3H, s), 0.70–2.10 [45H, m, including 0.87 (18H, s), 1.18 (3H, d, J 6)], 2.20 (1H, m), 2.44 (1H, m), 2.81 (1H, m), 3.79 (1H, m), 4.18 (1H, m), 4.36 (1H, m), 4.86 (1H, m), 5.17 (1H, m), 6.00 (1H, d, J 11), and 6.23 (1H, d, J 11); $\lambda_{max}$ 265 nm.

PREPARATION 42

Compound 47

The compound was prepared using Procedure 3 in which starting material III was compound 41. 47; $\delta$ (300 MHz) 0.06 (12H, m), 0.52 (3H, s), 0.60–2.10 [57H, m, including 0.87 (18H, s)], 2.20 (1H, m), 2.43 (1H, m), 2.81 (1H, m), 3.57 (1H, m), 4.18 (1H, m), 4.37 (1H, m), 4.86 (1H, m), 5.17 (1H, m), 6.00 (1H, d, J 11), and 6.23 (1H, d, J 11); $\lambda_{max}$ 265 nm.

PREPARATION 43

Compound 48

The compound was prepared using Procedure 3 in which starting material III was compound 42. 48; $\delta$ (300 MHz) 0.06 (12H, s), 0.53 (3H, s), 0.87 (18H, s), 1.0 (3H, d, J 7), 1.1–2.1 (27H, m, including 1.20 (6H, s)), 2.2 (1H, dd, J 13 and 7), 2.45 (1H, dd, J 13 and 4), 2.81 (1H, bd, J 11), 4.18 (1H, m), 4.35 (1H, m), 4.85 (1H, m), 5.16 (1H, m), 5.27 (2H, m), 6.01 (1H, d, J 11), 6.23 (1H, d, J 11); $\lambda_{max}$ 265 nm.

PREPARATION 44

Compound 49

The compound was prepared using Procedure 3 in which starting material III was compound 43. In this preparation the eluant used was 10% ether in petroleum ether. 49; $\delta$ (300 MHz) 0.05 (12H, m), 0.52 (3H, s), 0.60–2.10 [56H, m, including 0.82 (6H, t), 0.87 (18H, s), 0.90 (3H, d) and 1.45 (4H, q)], 2.20 (1H, m), 2.44 (1H, m), 2.81 (1H, m), 4.18 (1H, m), 4.36 (1H, m), 4.86 (1H, m), 5.17 (1H, m), 6.00 (1H, d, J 11), and 6.23 (1H, d, J 11).

PREPARATION 45

Compound 50

The compound was prepared using Procedure 3 in which starting material III was compound 44. In this preparation the eluant used was 10% ether in petroleum ether. 50; $\delta$ (300 MHz) 0.05 (12H, m), 0.52 (3H, s), 0.60–2.10 [60H, m, including 0.87 (18H, s)], 2.21 (1H, m), 2.43 (1H, m), 2.81 (1H, m), 4.18 (1H, m), 4.37 (1H, m), 4.86 (1H, m), 5.17 (1H, m), 6.00 (1H, d, J 11), and 6.23 (1H, d, J 11).

PREPARATION 46

Compound 57

The compound was prepared using Procedure 1 in which the side chain fragment A was compound 17 (0.42 g); 57; $\delta$ (300 MHz) 0.05 (12H, bs), 0.53 (3H, s), 0.85 (6H, t, J 7.5), 0.86 (9H, bs), 0.89 (9H, bs), 0.91 (3H, d, J 6), [0.98–2.10 (27H, m, including 1.45 (4H, q, J 7.5)], 2.30 (1H, m), 2.56 (1H, m), 2.86 (1H, m), 4.21 (1H, m), 4.52 (1H, m), 4.93 (1H, m), 4.98 (1H, m), 5.82 (1H, d, J 11), 6.45 (1H, d, J 11).

PREPARATION 47

Compound 58

The compound was prepared using Procedure 3 in which the starting material III was compound 57. 58 $\delta$ (300 MHz) 0.05 (12H, bs), 0.52 (3H, s), 0.8–2.1 [54H, m, including 0.84 (6H, t, J 7.5) and 0.87 (18H, s) and 1.45 (4H, q, J 7.5)], 2.20 (1H, m), 2.45 (1H, m), 2.80 (1H, m), 4.18 (1H, m), 4.36 (1H, m), 4.86 (1H, m), 5.16 (1H, m), 6.00 (1H, d, J 11), and 6.22 (1H, d, J 11).

PREPARATION 48

1-Bromo-4-propyl-4-trimethylsilyloxy-heptane (Compound 60)

The compound was prepared according to the procedure described in Preparation 7, except that the Grignard reagent was prepared from propylbromide (51 g), and the ethyl 4-bromopentanoate was substituted with ethyl 4-bromobutyrate (G, n=4) (23 g), via the intermediate carbinol H (n=2, $R^1=R^2=Pr$). The oily bromide (60) had b.p. 69°–70° C./1 mmHg and $\delta$ (300 MHz) 0.08 (9H, s), 0.88 (6H, t), 1.15–1.60 (10H, m), 1.85 (2H, m), and 3.39 (2H, t, J 6.8).

PREPARATION 49

1(S),3(R)-bis-tert-butyldimethylsilyloxy-20(S)-hydroxymethyl-9,10-secopregna-5(E), 7(E), 10)-triene (Compound 61)

A stirred, ice-cooled solution of the aldehyde 2 (5 g) in THF (20 ml) and ethanol (70 ml) was treated with sodium borohydride (0.35 g). After 10 minutes the reaction mixture was partitioned between ethylacetate and water, and the organic layer was washed with brine and dried. Concentration in vacuo gave the title compound, $\delta$ (300 MHz) 0.05 (12H, m), 0.56 (3H, s), 0.85 (9H, s), 0.89 (9H, s), 1.05 (3H, d, J 7), additionally 0.9–2.1 (15H, m), 2.31 (1H, bd), 2.55 (1H, dd, J 14 and 5), 2.87 (1H, bd), 3.38 (1H, dd, J 10 and 7), 3.65 (1H, dd, J 10 and 3), 4.21 (1H, m), 4.52 (1H, m), 4.93 (1H, bs), 4.98 (1H, bs), 5.82 (1H, d, J 11), and 6.45 (1H, d, J 11).

PREPARATION 50

1(S),3(R)-bis-tert-butyldimethylsilyloxy-20(S)-p-toluenesulphonyloxymethyl)-9,10-secopregna-5(E,7(E),10(19)-triene (Compound 62)

Compound 61 (5 g) was dissolved in dichloromethane (25 ml) and pyridine (3 ml), and the solution was stirred and ice-cooled during the addition of p-toluenesulphonyl chloride (2.5 g). The reaction mixture was allowed to stand at 5° C. overnight before being partitioned between ethyl acetate and water. The organic layer was washed consecutively with saturated copper sulphate solution (twice), water, 5% sodium hydrogen carbonate solution, and brine, and then dried and concentrated in vacuo. The residue was purified by chromatography (200 g silica gel; 5% ether in petroleum ether as eluant) followed by crystallization from ether-methanol to give the title compound as needles, δ (300 MHz) 0.05 (12H, m), 0.50 (2H, s), 0.85 (9H, s), 0.89 (9H, s), 0.99 (3H, d, J 7), 1-2.1 (14H, m), 2.29 (1H, bd), 2.44 (3H, s), 2.53 (1H, dd, J 14 and 5), 2.85 (1H, bd), 3.80 (1H, dd, J 9 and 6), 3.97 (1H, dd, J 9 and 3), 4.20 (1H, m), 4.51 (1H, m), 4.93 (1H, bs), 4.97 (1H, bs), 5.79 (1H, d, J 11), 6.42 (1H, d, J 11), 7.34 (2H, d, J 8), 7.78 (2H; d, J 8).

PREPARATION 51

Compound 63

To magnesium (0.21 g) a solution of compound 60 (2.63 g) in ether (5 ml) was added during 40 minutes, with stirring and heating to reflux. After a further 1 hour reflux, the Grignard reagent was separated from a small amount of unreacted magnesium and transferred to a dry flask under nitrogen. Dry THF (5 ml) was added with stirring, whereupon a white precipitate was formed. The mixture was cooled in an ice bath and a solution of lithium chloride (25 mg) and dry cupric chloride (40 mg) in dry THF (3 ml) was added with stirring during 5 minutes. Stirring in the ice bath was continued for a further 45 minutes. A solution of compound 62 (0.42 g) in dry THF (5 ml) was added during ca. 2 minutes, and stirring was continued for a further 40 minutes in the ice bath and then at room temperature for 17 hours.

The reaction mixture was partitioned between ether (25 ml) and aqueous ammonium chloride (1 g in 15 ml), and the aqueous phase was extracted twice with 25 ml portions of ether. The combined organic phase was washed with brine (10 ml), dried and concentrated in vacuo to give an oil which was purified by flash chromatography (40 g silica gel; petroleum ether, then 2.5% ether in petroleum ether as eluants) to give 63; δ (100 Hz) 0.08 (12H, s), 0.04–0.10 (9H, s), 0.54 (3H, s), 0.85 (9H, s), 0.90 (9H, s), 0.90 (6H, t), additionally 0.9–2.10 (33H, m), 2.30 (1H, bd), 2.56 (1H, dd), 2.86 (1H, d), 4.21 (1H, m), 4.53 (1H, m), 4.93 (1H, m), 4.98 (1H, m), 5.82 (1H, d, J 11.5), and 6.45 (1H, d, J 11.5).

PREPARATION 52

Compound 64

A mixture of anthracene (0.18 g), triethylamine (75 mg), and compound 63 (0.48 g) in methylene chloride (35 ml), stirred under an atmosphere of nitrogen in a Pyrex flask immersed in a water bath at 20° C., was illuminated with radiation from a high pressure Hg lamp (type: Hanau TQ 718Z2) for 1 hour. The reaction mixture was filtered and concentrated in vacuo to give a residue. This was purified by flash chromatography (65 g silica gel; 1% ether in petroleum ether as eluant) to give 64; δ (100 MHz) 0.08 (12H, s), 0.05–0.10 (9H, s), 0.52 (3H, s), 0.87 (18H, s), 0.84–0.94 (9H, m), 1.00–2.10 (30H, m), 2.21 (1H, dd), 2.44 (1H, dd), 2.79 (1H, d), 4.18 (1H, m), 4.37 (1H, m), 4.86 (1H, m), 5.17 (1H, m), 6.01 (1H, d, J 11.2), and 6.23 (1H, d, J 11.2).

PREPARATION 53

1(S),3(R)-Di-tert-butyldimethylsilyloxy-20(R)-(6'-methyl-1-heptyl)-9,10-secopregna-5(E),7(E),10(19)-triene (Compound 66—the side chain desoxyanalogue of Compound 25)

The stirred Grignard reagent obtained from 5-methyl-1-hexyl bromide (2.09 g) and magnesium (0.29 g) in dry THF (8 ml) was treated at 0° C. with a solution of lithium chloride (14 mg) and anhydrous cupric choride (22 mg) in dry THF (1.6 ml) followed by a solution of Compound 62 (0.25 g) in dry THF (1 ml): After 1 hour, the reaction mixture was partitioned between water and ether, and the ether layer was washed with brine, dried and concentrated in vacuo. Purification of the residue by chromatography (15 g silica gel, 2% ether in petroleum ether as eluant) followed by crystallisation from ether-methanol gave the title compound, δ (300 MHz) 0.07 (12H, m), 0.55 (3H, s), 0.87 (9H, s), 0.87 (3H, d), 0.9 (9H, s), additionally 0.85–2.1 (31H, m), 2.31 (1H, bd), 2.57 (1H, dd, J 14 and 5), 2.87 (1H, bd), 4.22 (1H, m), 4.54 (1H, m), 4.94 (1H, bs), 4.99 (1H, bs), 5.83 (1H, d, J 11), 6.47 (1H, d, J 11).

PREPARATION 54

1(S),3(R)-Bis-tert-butyldimethylsilyloxy-20(R)-(6'-methyl-1-heptyl)-9,10-secopregna-5(Z),7(E),10(19)-triene (Compound 67—the side chain desoxyanalogue of Compound 30)

The compound was prepared using Procedure 3 in which the starting material (substituting compound III) was Compound 66 (see Preparation 53).

In this preparation the eluant was 2% ether in petroleum ether. The product gave the expected spectroscopic data.

EXAMPLE 1

1(S),3(R)-Dihydroxy-20(R)-[3-(1-hydroxycyclopropyl)propyl]-9,10-secopregna-5-(Z),7(E),10(19)-triene (Compound 34)

A solution of the compound 28 (50 mg) and tetra-n-butylammonium fluoride trihydrate (0.1 g) in THF (5 ml) was heated at 60° C. under an atmosphere of nitrogen for 50 minutes. After cooling, the reaction solution was partitioned between ethyl acetate (40 ml) and 2% sodium hydrogen carbonate solution (30 ml), and the organic layer was washed with water and brine, dried and concentrated in vacuo to give a crude product containing compound 33. This was dissolved in ethanol (3 ml) and pyridinium p-toluenesulphonate (9 mg) added. The stirred solution was then heated at 50° C. under an atmosphere of nitrogen for 30 minutes. After cooling, the reaction solution was partitioned between ethyl acetate (30 ml) and water. The organic layer was washed consecutively with 5% sodium hydrogen carbonate solution and brine, dried, and concentrated in vacuo. The residue was purified by chromatography (15 g silica gel; ethyl acetate as eluant) to give 34; (300 MHz) 0.42 (2H, m), 0.53 (3H, s), 0.72 (2H, m), 0.93 (3H, d, J 6), 1–2.05 (23H, m), 2.30 (1H, dd, J 13 and 6), 2.59 (1H, dd, J 13 and 3), 2.81 (1H, dd, J 12 and 4), 4.22 (1H, m), 4.42 (1H, m), 4.99 (1H, bs), 5.32 (1H, bs), 6.00 (1H, d, J 11), 6.37 (1H, d, J 11); $\lambda_{max}$ 265 nm.

PROCEDURE 4

Preparation of Compound I from the Corresponding Compound IV

A solution of the compound IV (0.2 g) and tetra-n-butylammonium fluoride trihydrate (0.4 g) in THF (10 ml) was heated at 60° C. under an atmosphere of nitrogen for 50 minutes. After cooling, the reaction solution was partitioned between ethyl acetate (40 ml) and 2% sodium hydrogen carbonate solution (30 ml), and the organic layer was washed with water and brine, dried and concentrated. The residue was purified by chromatography (30 g silica gel, ethyl acetate as eluant) to give I.

The compounds of Examples 2, 3, 4, 5, 6, 7, 8, 9, 10, 11 and 12 and 14 were prepared using procedure 4 in which starting material IV was respectively compounds 29, 30, 31, 32, 45, 46, 47, 48, 49, 50, 58, and 67 (See Preparation 54).

EXAMPLE 2

1(S),3(R)-Dihydroxy-20(R)-[3-(1-hydroxycyclohexyl)-propyl]-9,10-secopregna-5(Z),7(E),10(19)-triene (Compound 35)

$\delta$ (300 MHz) 0.53 (3H, s), 0.92 (3H, d, J 6), 1–2.1 (33H, m), 2.30 (1H, dd, J 13 and 7), 2.59 (1H, dd, J 13 and 3), 2.81 (1H, dd, J 12 and 3), 4.21 (1H, m), 4.42 (1H, m), 4.99 (1H, bs), 5.32 (1H, bs), 6.00 (1H, d, J 11), 6.37 (1H, J 11); $\lambda_{max}$ 265 nm.

EXAMPLE 3

1(S),3(R)-Dihydroxy-20(R)-(6-hydroxy-6-methyl-1-heptyl)-9,10-secopregna-5(Z),7(E),10(19)-triene (Compound 36)

$\delta$ (300 MHz) 0.54 (3H, s), 0.92 (3H, d, J 6), 0.85–2.1 (33H, m, including 1.21 (6H, s)), 2.31 (1H, dd, J 13 and 6), 2.60 (1H, dd, J 13 and 3), 2.82 (1H, dd, J 12 and 3), 4.23 (1H, m), 4.43 (1H, m), 5.00 (1H, bs), 5.33 (1H, bs), 6.02 (1H, d, J 11), 6.38 (1H, J 11); $\lambda_{max}$ 265 nm.

EXAMPLE 4

1(S),3(R)-Dihydroxy-20(R)-(7-hydroxy-7-methyl-1-octyl)-9,10-secopregna-5(Z),7(E),10(19)-triene (Compound 37)

$\delta$ (300 MHz) 0.53 (3H, s), 0.90 (3H, d, J 6), 0.9–2.05 (35H, m, including 1.20 (6H, s)), 2.28 (1H, dd, J 13 and 7), 2.59 (1H, dd, J 13 and 3), 2.82 (1H, dd, J 11 and 3), 4.22 (1H, m), 4.41 (1H, m), 4.99 (1H, bs), 5.32 (1H, bs), 6.01 (1H, d, J 11), 6.37 (1H, d, J 11); $\lambda_{max}$ 265 nm.

EXAMPLE 5

1(S),3(R)-Dihydroxy-20(R)-(7-hydroxy-7-methyloct-1(E)-en-1-yl-9,10-secopregna-5(Z),7(E),10(19)-triene Compound 38

$\delta$ (300 MHz) 0.54 (3H, s), 1.0 (3H, d, J 7), 1.1–2.1 (31H, m, including 1.20 (6H, dd, J 13 and 7), 2.60 (1H, dd, J 13 and 3), 2.82 (1H, dd, J 11 and 3), 4.22 (1H, m), 4.42 (1H, m), 5.00 (1H, bs), 5.25 (2H, m), 5.31 (1H, bs), 6.01 (1H, d, J 11), 6.37 (1H, d, J 11); $\lambda_{max}$ 265 nm.

EXAMPLE 6

1(S),3(R)-Dihydroxy-20(R)-(4(S)-hydroxy-1-pentyl)-9,10-secopregna-5(Z),7(E),10(19)-triene (Compound 51)

$\delta$ (300 MHz) 0.53 (3H, s), 0.60–2.10 [29H, m, including 1.18 (3H, d, J 6], 2.30 (1H, m), 2.59 (1H, m), 2.81 (1H, m), 3.78 (1H, m), 4.21 (1H, m), 4.42 (1H, m), 4.99 (1H, m), 5.31 (1H, m), 6.00 (1H, d, J 11) and 6.36 (1H, d, J 11); $\lambda_{max}$ 265 nm.

EXAMPLE 7

1(S),3(R)-Dihydroxy-20(R)-(4(R)-hydroxy-1-pentyl)-9,10-secopregna-5(Z),7(E),10(19)-triene (Compound 52)

$\delta$ (300 MHz) 0.53 (3H, s), 0.60–2.10 [29H, m, including 1.18 (3H, d, J 6)], 2.30 (1H, m), 2.59 (1H, m), 2.81 (1H, m), 3.78 (1H, m), 4.21 (1H, m), 4.42 (1H, m), 4.99 (1H, m), 5.31 (1H, m), 6.00 (1H, d, J 11) and 6.36 (1H, d, J 11); $\lambda_{max}$ 265 nm.

EXAMPLE 8

1(S),3(R)-Dihydroxy-20(R)-(4(R)-hydroxy-1-undecyl)-9,10-secopregna-5(Z),7(E),10(19)-triene (Compound 53)

$\delta$ (300 MHz) 0.53 (3H, s), 0.60–2.10 [41H, m, including 0.89 (3H, t), 0.94 (3H, d, J 6)], 2.30 (1H, m), 2.59 (1H, m), 2.81 (1H, m), 3.57 (1H, m), 4.21 (1H, m), 4.41 (1H, m), 4.99 (1H, m), 5.31 (1H, m), 6.00 (1H, d, J 11) and 6.37 (1H, d, J 11); $\lambda_{max}$ 265 nm.

EXAMPLE 9

1(S),3(R)-Dihydroxy-20(R)-(6-hydroxy-6-methylhept-1(E)-en-1-yl-9,10-secopregna-5(Z),7(E),10(19)-triene (Compound 54)

$\delta$ (300 MHz) 0.54 (3H, s), 1.0 (3H, d, J 7), 1.1–2.1 (29H, m, including 1.19 (6H, s)), 2.29 (1H, dd, J 13 and 7), 2.58 (1H, dd, J 13 and 3), 2.81 (1H, dd, J 11 and 3), 4.2 (1H, m), 4.40 (1H, m), 4.98 (1H, bs), 5.25 (2H, m), 5.31 (1H, bs), 6.00 (1H, d, J 11), 6.35 (1H, d, J 11); $\lambda_{max}$ 265 nm.

EXAMPLE 10

1(S),3(R)-Dihydroxy-20(R)-(6-ethyl-6-hydroxy-1-octyl)-9,10-secopregna-5(Z),7(E),10(19)-triene (Compound 55)

$\delta$ (300 MHz) 0.52 (3H, s), 0.60–2.10 [40H, m, including 0.84 (6H, t, J 7.5), 0.90 (3H, d, J 6), 1.44 (4H, q, J 7.5)], 2.29 (1H, m), 2.58 (1H, m), 2.81 (1H, m), 4.21 (1H, m), 4.41 (1H, m), 4.99 (1H, m), 5.31 (1H, m), 6.00 (1H, d, J 11) and 6.36 (1H, d, J 11); $\lambda_{max}$ 265 nm.

EXAMPLE 11

1(S),3(R)-Dihydroxy-20(R)-(6-hydroxy-6-propyl-1-nonyl)-9,10-secopregna-5(Z),7(E),10(19)-triene (Compound 56)

$\delta$ (300 MHz) 0.54 (3H, s), 0.60–2.10 (44H, m), 2.31 (1H, m), 2.61 (1H, m), 2.82 (1H, m), 4.23 (1H, m), 4.43 (1H, m), 5.01 (1H, m)), 5.33 (1H, m), 6.02 (1H, d, J 11), 6.38 (1H, d, J 11); $\lambda_{max}$ 264 nm.

EXAMPLE 12

1(S),3(R)-Dihydroxy-20(R)-(5-ethyl-5-hydroxy-1-heptyl)-9,10-secopregna-5(Z),7(E),10(19)-triene (Compound 59)

δ (300 MHz) 0.53 (3H, s), 0.85 (6H, t, J 7.5), 0.90 (3H, d, J 6), 0.98–2.10 [29H, m, including 1.45 (4H, q, J 7.5), 2.30 (1H, m), 2.59 (1H, m), 2.81 (1H, m), 4.21 (1H, m), 4.42 (1H, m), 4.99 (1H, m), 5.32 (1H, m), 6.00 (1H, d, J 11) and 6.37 (1H, d, J 11).

EXAMPLE 13

1(S),3(R)-Dihydroxy-20(R)-(5-propyl-5-hydroxy-1-octyl)-9,10-secopregna-5(Z),7(E),10(19)-triene (Compound 65)

A solution of compound 64 (0.38 g) in a mixture of ethyl acetate (20 ml), acetonitrile (33 ml) and ca. 40% aqueous hydrogen fluoride (1 ml) was stirred under nitrogen for 1 hour at 25° C. The reaction solution was partitioned between ethyl acetate (100 ml) and 2% sodium bicarbonate solution (50 ml). The organic phase was extracted twice with 50 ml-portions of water and with brine (25 ml), dried and concentrated in vacuo to give an oil.

This was purified by flash cromatography, twice. Firstly on silica gel (100 g) with ethyl acetate as eluant, secondly on silica gel (40 g) with 30% petroleum ether in ethyl acetate as eluant. The product 65 was obtained as an oil; δ (300 MHz) 0.54 (3H, s), 0.92 (6H, t), 0.88–0.95 (3H, d), 1.00–2.10 (33H, m), 2.31 (1H, dd), 2.60 (1H, dd), 2.82 (1H, dd), 4.23 (1H, m), 4.43 (1H, m), 5.00 (1H, m), 5.33 (1H, m), 6.02 (1H, d, J 11.3), and 6.38 (1H, d, J 11.3).

EXAMPLE 14

1(S),3(R)-Dihydroxy-20(R)-(6'-methyl-1'-heptyl)-9,10-secopregna-5(Z),7(E),10(19)-triene (Compound 68)

δ (300 MHz) 0.53 (3H, s), 0.85 (6H, d), 0.91 (3H, d), additionally 0.9–2.0 (27H, m), 2.27 (1H, dd), 2.57 (1H, m), 2.80 (1H, m), 4.20 (1H, m), 4.40 (1H, m), 4.99 (1H, bs), 5.31 (1H, bs), 6.00 (1H, d, J 11), and 6.36 (1H, d, J 11).

EXAMPLE 15

Dermatological Cream Containing Compound 36

In 1 g almond oil was dissolved 1 mg 36. To this solution was added 40 g of mineral oil and 20 g of self-emulsifying beeswax. The mixture was heated to liquify. After the addition of 40 ml hot water, the mixture was mixed well. The resulting cream contains approximately 10 μg of 36 per gram of cream.

EXAMPLE 16

Capsules containing Compound 36

26 was suspended in arachis oil to a final concentration of 50 μg 36/ml oil. 10 Parts by weight of gelatine, 5 parts by weight glycerine, 0.08 parts by weight potassium sorbate, and 14 parts by weight distilled water were mixed together with heating and formed into soft gelatine capsules. These were then filled each with 100 μl of the 36 in oil suspension, such that each capsule contained 5 μg 36.

What we claim is:

1. A compound of the formula I

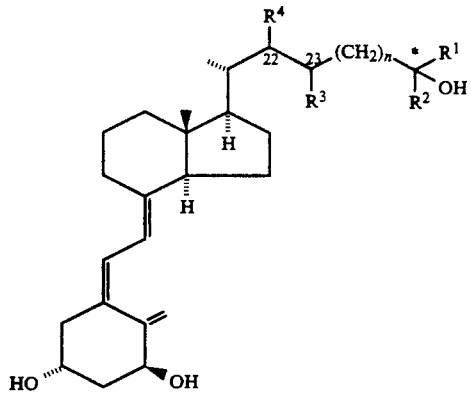

in which formula n is an integer from 1–7; and $R^1$ and $R^2$, which may be the same or different, stand for hydrogen, or straight or branched, saturated or unsaturated $C_1$–$C_7$-alkyl; with the provisos that when n=1, $R^1$ and $R^2$ cannot simultaneously be hydrogen, nor can $R^1$ and $R^2$ simultaneously be an alkyl group independently chosen from methyl, ethyl and normal-propyl, and when n=2, $R^1$ and $R^2$ cannot simultaneously be methyl; or $C_3$–$C_8$-cyclo-alkyl, or, taken together with the carbon (starred in formula I) bearing the hydroxyl group, $R^1$ and $R^2$ can form a saturated or unsaturated $C_3$–$C_9$ carbocyclic ring; and $R^3$ and $R^4$ represent either both hydrogen, or when taken together constitute a bond, such double bond (either in the Z or E configuration) connecting carbons numbered 22 and 23; and derivatives of the compounds of formula I in which one or more hydroxy groups have been transformed into -O-acyl or -O-glycosyl or phosphate ester groups, such masked groups being hydrolyzable in vivo, or derivatives of the compounds of formula I in which the hydroxyl group at the starred carbon atom is lacking, these compounds being converted to active compounds of formula I by enzymatic hydroxylation after administration.

2. A diastereoisomer of a compound according to claim 1, in pure form; or a mixture of diastereoisomers of a compound according to claim 1.

3. A compound according to claim 1, selected from the group consisting of
1(S),3(R)-Dihydroxy-20(R)-(5-ethyl-5-hydroxy-1-heptyl)-9,10-secopregna-5(Z),7(E),10(19)-triene;
1(S),3(R)-Dihydroxy-20(R)-(6-hydroxy-6-methyl-1-heptyl)-9,10-secopregna-5(Z),7(E),10(19)-triene;
1(S),3(R)-Dihydroxy-20(R)-(6-hydroxy-6-methylhept-1(E)-en-1-yl-9,10)-secopregna-5(Z),7(E),10(19)-triene;
1(S),3(R)-Dihydroxy-20(R)-(6-ethyl-6-hydroxy-1-octyl)-9,10)-secopregna-5(Z),7(E),10(19)-triene;
1(S),3(R)-Dihydroxy-20(R)-(7-hydroxy-7-methyl-1-octyl)-9,10)-secopregna-5(Z),7(E),10(19)-triene;
1(S),3(R)-Dihydroxy-20(R)-(7-hydroxy-7-methyloct-1(E)-en-1-yl-9,10)-secopregna-5(Z),7(E),10(19)-triene;
1(S),3(R)-Dihydroxy-20(R)-(6'-methyl-1'-heptyl)-9,10-secopregna-5(Z),7(E),10(19)-triene.

4. A pharmaceutical composition containing a pharmaceutically effective amount of one or more of the compounds of claim 1, together with pharmaceutically acceptable, non-toxic carriers or auxiliary agents.

5. A pharmaceutical composition according to claim 4 in dosage unit form.

6. A dosage unit according to claim 5 containing from 0.5–500 μg of a compound of formula I.

7. A method for the treatment of diabetes mellitus, hypertension, imbalance in the immune system, inflammatory diseases and diseases characterized by abnormal cell differentiation or cell proliferation which comprises administering an effective amount of a composition according to claim 6 to a human or animal in need of such treatment.

8. A method according to claim 7 for prevention of graft rejection, in which, additionally, the human or animal is subjected to a cyclosporin treatment.

9. A dosage unit according to claim 6 containing from 1–250 μg of said compound.

10. A method according to claim 7 wherein the disease treated is psoriasis.

* * * * *